United States Patent [19]
Patterson et al.

[11] Patent Number: 5,941,869
[45] Date of Patent: Aug. 24, 1999

[54] APPARATUS AND METHOD FOR CONTROLLED REMOVAL OF STENOTIC MATERIAL FROM STENTS

[75] Inventors: Greg R. Patterson, Pleasanton; G. Ronald Williams, Menlo Park; James J. Leary, Sunnyvale, all of Calif.

[73] Assignee: Prolifix Medical, Inc., Palo Alto, Calif.

[21] Appl. No.: 08/857,659

[22] Filed: May 16, 1997

Related U.S. Application Data

[63] Continuation-in-part of application No. 08/798,722, Feb. 12, 1997, Pat. No. 5,882,329.

[51] Int. Cl.$^6$ .................................................. A61M 31/00
[52] U.S. Cl. ........................... 604/508; 604/22; 604/503; 606/159; 606/198
[58] Field of Search ...................................... 604/503, 507, 604/508, 500, 510, 22; 600/264, 280, 568, 570, 571; 606/159, 198, 200

[56] References Cited

U.S. PATENT DOCUMENTS

| | | |
|---|---|---|
| 4,273,128 | 6/1981 | Lary . |
| 4,445,509 | 5/1984 | Auth . |

(List continued on next page.)

FOREIGN PATENT DOCUMENTS

| | | |
|---|---|---|
| 39 21 071 C2 | 2/1991 | Germany . |
| 9400027 | 1/1995 | Netherlands . |
| WO 95/29626 | 11/1995 | WIPO . |
| WO 97/17889 | 5/1997 | WIPO . |

OTHER PUBLICATIONS

Moris, M.D., Cesar et al. "Stenting for coronary dissection after balloon dilation of in–stent restenosis: Stenting a previously stented site," *Am Heart J*, 131:834–836 (1996).
Ghannem, M. et al. "Restenose Sur Endoprothese Coronaire: Traitement Par Implnation D'Une Nouvelle Endoprothese," *Ann. Cardiol. Angeol.*, 45(5):287–290 (1996).
Khanolkar, UB "Percutaneous Transluminal Rotational Atherectomy for Treatment of In–stent Restenosis," *Indian Heart J*, 48:281–282 (1996).
Schomig, M.D., Albert, et al. "Emergency Coronary Stenting for Dissection During Percutaneous Transluminal Coronary Angioplasty: Angiographic Follow–Up After Stenting and After Repeat Angioplasty of the Stented Segment," *JACC*, 23(5):1053–1060 (1994).

(List continued on next page.)

*Primary Examiner*—Wynn Wood Coggins
*Assistant Examiner*—Deborah Blyveis
*Attorney, Agent, or Firm*—Townsend&Townsend&Crew LLP

[57] ABSTRACT

Apparatus and methods for treating in-stent restenosis are described for removing stenotic material from within previously stented regions of a patient's vasculature. The apparatus includes a catheter system having a stenotic material removal mechanism mounted on a distal portion of an elongated inner catheter. A sensing means, such as one or more sensing electrodes, are positioned on an outer surface of the apparatus. In addition, the apparatus optionally includes control means for diametrically expanding the stenotic material removal mechanism for effective recanalization of the stent. A coaxial outer catheter is provided for aspirating stenotic material which is removed from within the stent. In addition, embolic filter apparatus are described for collecting the stenotic material removed from within the stent. The methods comprise operating the stenotic material removal mechanism within a body vessel, typically a coronary artery or other artery, which has become restenosed or otherwise occluded following the initial stent placement, and sensing the proximity or contact between the stenotic material removal mechanism and the stent within the arterial wall so that the stenosis can be effectively recanalized without damaging the stent. The sensing means may be used to indicate an unsafe condition that might lead to stent damage, in response to which, the stenotic material removal mechanism may be manually or automatically deactivated.

25 Claims, 12 Drawing Sheets

U.S. PATENT DOCUMENTS

| | | |
|---|---|---|
| 4,653,496 | 3/1987 | Bundy et al. . |
| 4,696,667 | 9/1987 | Masch . |
| 4,706,671 | 11/1987 | Weinrib . |
| 4,723,549 | 2/1988 | Wholey et al. . |
| 4,728,319 | 3/1988 | Masch . |
| 4,732,154 | 3/1988 | Shiber . |
| 4,790,812 | 12/1988 | Hawkins, Jr. et al. . |
| 4,792,130 | 12/1988 | Fogarty et al. . |
| 4,794,931 | 1/1989 | Yock . |
| 4,819,634 | 4/1989 | Shiber . |
| 4,842,579 | 6/1989 | Shiber . |
| 4,850,957 | 7/1989 | Summers . |
| 4,857,045 | 8/1989 | Rydell . |
| 4,857,046 | 8/1989 | Stevens et al. . |
| 4,867,156 | 9/1989 | Stack et al. . |
| 4,883,458 | 11/1989 | Shiber . |
| 4,886,061 | 12/1989 | Fischell et al. . |
| 4,890,611 | 1/1990 | Monfort et al. . |
| 4,894,051 | 1/1990 | Shiber . |
| 4,895,560 | 1/1990 | Papantonakos . |
| 4,926,858 | 5/1990 | Gifford, III et al. . |
| 4,966,604 | 10/1990 | Reiss . |
| 4,979,939 | 12/1990 | Shiber . |
| 4,979,951 | 12/1990 | Simpson . |
| 5,000,185 | 3/1991 | Yock . |
| 5,009,659 | 4/1991 | Hamlin et al. . |
| 5,011,488 | 4/1991 | Ginsburg . |
| 5,011,489 | 4/1991 | Salem . |
| 5,011,490 | 4/1991 | Fischell et al. . |
| 5,041,082 | 8/1991 | Shiber . |
| 5,071,424 | 12/1991 | Reger . |
| 5,074,040 | 12/1991 | Simpson et al. . |
| 5,078,723 | 1/1992 | Dance et al. . |
| 5,085,662 | 2/1992 | Willard . |
| 5,087,265 | 2/1992 | Summers . |
| 5,100,424 | 3/1992 | Jang et al. . |
| 5,116,352 | 5/1992 | Schnepp-Pesch et al. . |
| 5,135,483 | 8/1992 | Wagner et al. . |
| 5,154,724 | 10/1992 | Andrews . |
| 5,158,564 | 10/1992 | Schnepp-Pesch et al. . |
| 5,160,342 | 11/1992 | Reger et al. . |
| 5,176,693 | 1/1993 | Pannek, Jr. . |
| 5,192,291 | 3/1993 | Pannek, Jr. . |
| 5,195,954 | 3/1993 | Schnepp-Pesch et al. . |
| 5,196,024 | 3/1993 | Barath . |
| 5,209,749 | 5/1993 | Buelna . |
| 5,217,474 | 6/1993 | Zacca et al. . |
| 5,224,945 | 7/1993 | Pannek, Jr. . |
| 5,234,451 | 8/1993 | Osypka . |
| 5,269,751 | 12/1993 | Kaliman . |
| 5,308,354 | 5/1994 | Zacca et al. . |
| 5,314,438 | 5/1994 | Shturman . |
| 5,318,576 | 6/1994 | Plassche, Jr. et al. . |
| 5,320,634 | 6/1994 | Vigil et al. . |
| 5,334,211 | 8/1994 | Shiber . |
| 5,356,418 | 10/1994 | Shturman . |
| 5,360,432 | 11/1994 | Shturman . |
| 5,370,653 | 12/1994 | Cragg . |
| 5,376,100 | 12/1994 | Lefebvre . |
| 5,383,460 | 1/1995 | Jang et al. . |
| 5,402,790 | 4/1995 | Jang et al. . |
| 5,427,115 | 6/1995 | Rowland et al. . |
| 5,429,136 | 7/1995 | Milo et al. . |
| 5,443,443 | 8/1995 | Shiber . |
| 5,490,859 | 2/1996 | Mische et al. . |
| 5,527,326 | 6/1996 | Hermann et al. . |
| 5,535,756 | 7/1996 | Parasher . |
| 5,540,707 | 7/1996 | Ressemann et al. . |
| 5,554,163 | 9/1996 | Shturman . |
| 5,556,405 | 9/1996 | Lary . |
| 5,556,408 | 9/1996 | Farhat . |
| 5,569,276 | 10/1996 | Jang et al. . |
| 5,578,018 | 11/1996 | Rowland et al. . |
| 5,643,297 | 7/1997 | Nordgren et al. . |
| 5,695,506 | 12/1997 | Pike et al. . |
| 5,749,848 | 5/1998 | Jang et al. . |

OTHER PUBLICATIONS

Macander, M.D., Ph.D., Peter J., et al. "Balloon Angioplasty for Treatment of In–Stent Restenosis: Feasibility, Safety, and Efficacy," *Catheterization and Cardiovascular Diagnosis*, 32:125–131 (1994).

Gordon, M.D., Paul C. "Mechanisms of Restenosis and Redilation Within Coronary Stents–Quantitative Angiographic Assessment," *JACC*, 21(5):1166–1174 (1993).

Baim, M.D., Donald S. "Management of Restenosis Within the Palmaz–Schatz Coronary Stent (The U.S. Multicenter Experience)," *The American Journal of Caridiology*, 71:364–366 (1993).

Strauss, M.D., Bradley H., "Directional Atherectomy for Treatment of Restenosis Within Coronary Stents: Clinical, Angiographic and Histologic Results," *JACC*, 20(7):1465–1473 (1992).

Bowerman, M.D., Richard E., "Disruption of a Coronary Stent During Atherectomy for Restenosis," *Catheterization and Cardiovascular Diagnosis*, 24:248–251 (1991).

Haude, Michael et al. "Treatment of In–Stent Restenosis," Chapter 52, pp. 357–365.

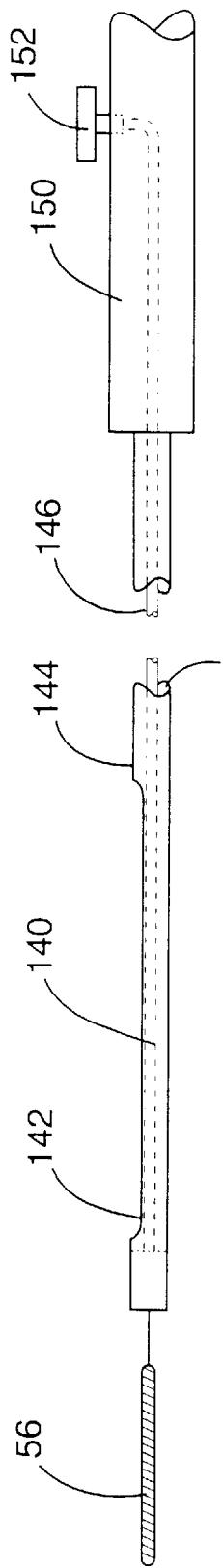
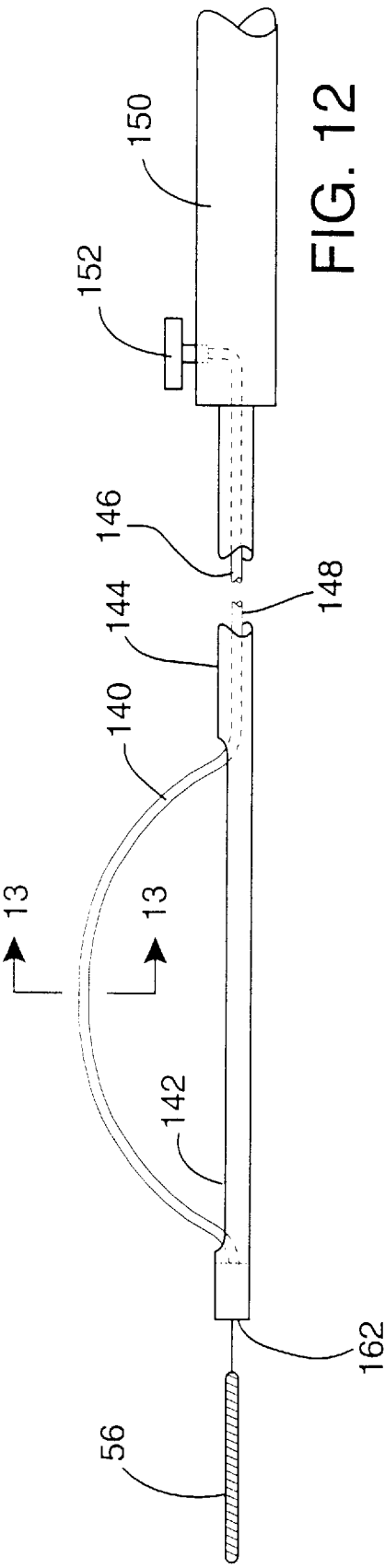
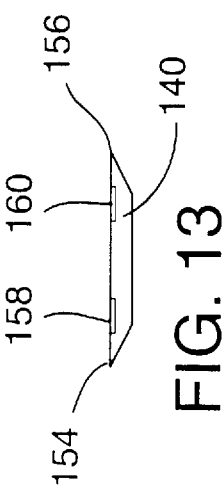

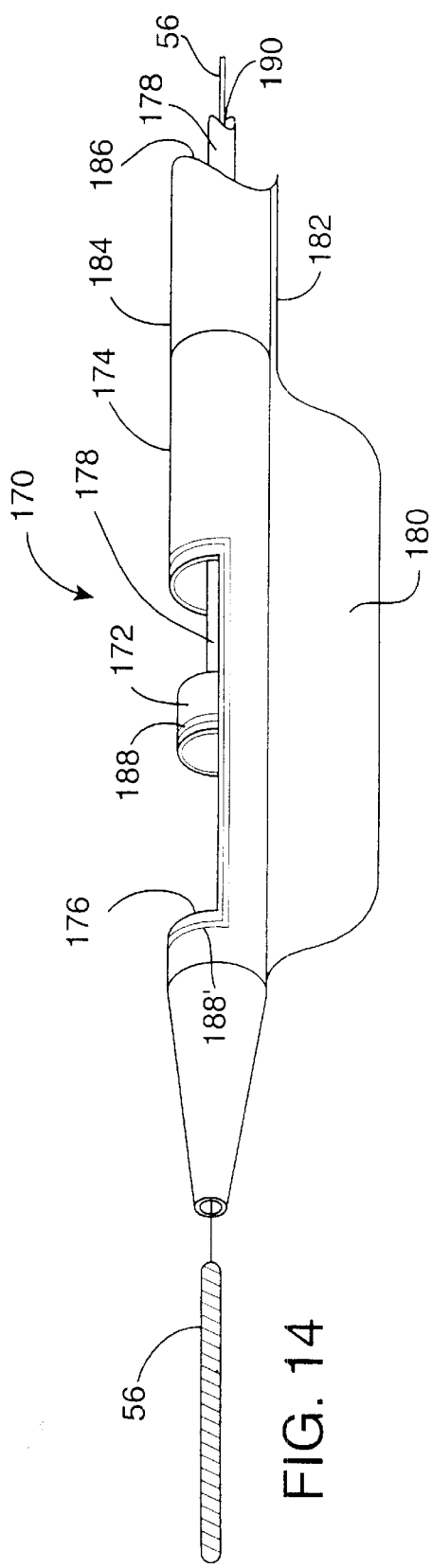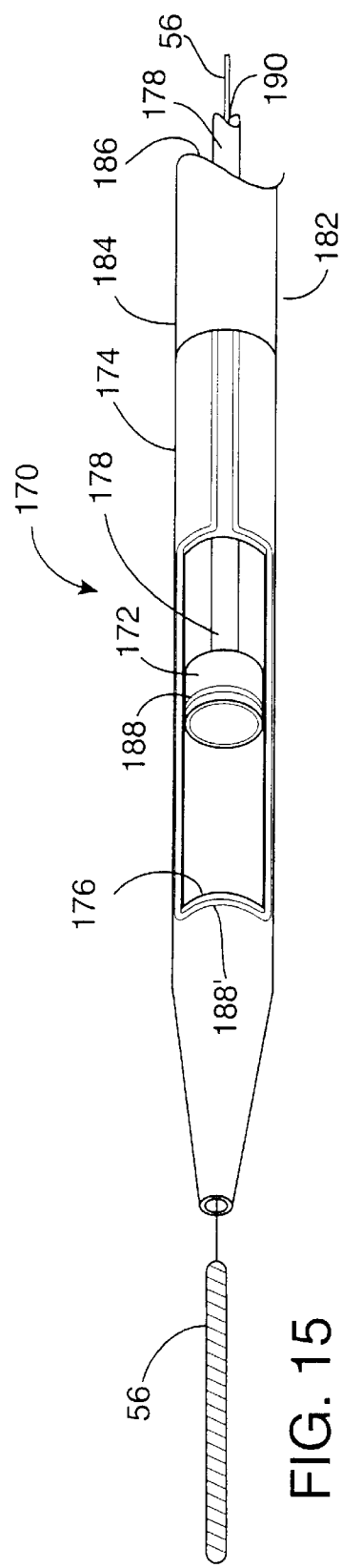

APPARATUS AND METHOD FOR CONTROLLED REMOVAL OF STENOTIC MATERIAL FROM STENTS

RELATIONSHIP TO OTHER PATENT APPLICATIONS

This patent application is a continuation-in-part of co-owned, patent application Ser. No. 08/798,722, U.S. Pat. No. 5,882,329 filed Feb. 12, 1997, the entire disclosure of which is hereby incorporated herein by reference.

BACKGROUND OF THE INVENTION

1. Field of the Invention

The present invention relates generally to apparatus and methods for removing occluding material from stented regions within blood vessels which have restenosed. More particularly, the present invention relates to apparatus and methods for sensing a stent within the wall of a restenosed blood vessel and removing the occluding material without damaging the stent.

Percutaneous transluminal angioplasty (PTA) and percutaneous transluminal coronary angioplasty (PTCA) procedures are widely used for treating stenotic atherosclerotic regions of a patient's vasculature to restore adequate blood flow. Catheters having an expansible distal end, typically in the form of an inflatable balloon, are positioned in an artery, such as a coronary artery, at a stenotic site. The expansible end is then expanded to dilate the artery in order to restore adequate blood flow to regions beyond the stenosis. While PTA and PTCA have gained wide acceptance, these angioplasty procedures suffer from two major problems: abrupt closure and restenosis.

Abrupt closure refers to rapid reocclusion of the vessel within hours of the initial treatment, and often occurs in patients who have recently suffered acute myocardial infarction. Abrupt closure often results from either an intimal dissection or from rapid thrombus formation which occurs in response to injury of the vascular wall from the initial angioplasty procedure. Restenosis refers to a renarrowing of the artery over the weeks or months following an initially apparently successful angioplasty procedure. Restenosis occurs in up to 50% of all angioplasty patients and results at least in part from smooth muscle cell proliferation and migration.

Many different strategies have been proposed to ameliorate abrupt closure and reduce the rate of restenosis. Of particular interest to the present invention, the implantation of vascular stents following angioplasty has become widespread. Stents are thin-walled tubular scaffolds which are expanded in the arterial lumen following the angioplasty procedure. Most commonly, the stents are formed from a malleable material, such as stainless steel, and are expanded in situ using a balloon. Alternatively, the stents may be formed from a shape memory alloy or other elastic material, in which case they are allowed to self-expand at the angioplasty treatment site. In either case, the stent acts as a mechanical support for the artery wall, inhibiting abrupt closure and reducing the restenosis rate as compared to PTCA.

While stents have been very successful in inhibiting abrupt closure and reasonably successful in inhibiting restenosis, a significant portion of the treated patient population still experiences restenosis over time. Most stent structures comprise an open lattice, typically in a diamond or spiral pattern, and cell proliferation (also referred to as intimal hyperplasia) can intrude through the interstices between the support elements of the lattice. As a result, instead of forming a barrier to hyperplasia and restenosis, the stent can become embedded within an accumulated mass of thrombus and tissue growth, and the treatment site once again becomes occluded.

To date, proposed treatments for restenosis within previously stented regions of the coronary and other arteries have included both follow-up balloon angioplasty and directional atherectomy, e.g. using the Simpson directional atherectomy catheter available from Guidant Corporation, Santa Clara, Calif. Neither approach has been wholly successful. Balloon angioplasty can temporarily open the arterial lumen, but rarely provides long-term patency. Directional atherectomy can successfully debulk the lumen within the stent, but typically does not fully restore the stented lumen to its previous diameter because the catheter removes the stenotic material in an asymmetric pattern. Moreover, it has been found that the atherectomy cutting blades can damage the implanted stent. Such adverse effects were reported by Bowerman et al. in *Disruption of a coronary stent during atherectomy for restenosis* in the December 1991 issue of Catheterization and Cardiovascular Diagnosis and by Meyer et al. in *Stent wire cutting during coronary directional atherectomy* in the May 1993 issue of Clinical Cardiology. The possibility of such adverse outcomes is likely to limit the application of atherectomy as a treatment for stent restenosis and will probably result in more tentative use of the atherectomy cutter within the stented region when it is applied, leading to less complete removal of the stenosis.

For these reasons, it would be desirable to provide improved methods for treating restenosis within regions of the vasculature which have previously been implanted with stents. More particularly, it would be desirable to provide an apparatus for removal of stenotic material from within a stent which includes a sensing means for sensing when the stenosis removal mechanism is approaching or contacting the stent within the arterial wall so that the occluded artery can be effectively recanalized without damaging the stent. The stenosis removal mechanism of the apparatus may advantageously be a directional cutting or debulking device for selectively removing the stenotic material from within a stent or it may be a symmetrical cutting or debulking device for removing the stenotic material uniformly from the entire inner periphery of the stent.

2. Description of the Background Art

Post-angioplasty restenosis is discussed in the following publications: Khanolkar (1996) *Indian Heart J.* 48:281–282; Ghannem et al. (1996) *Ann. Cardiol. Angeiol.* 45:287–290; Macander et al. (1994) *Cathet. Cardiovasc. Diagn.* 32:125–131; Strauss et al. (1992) *J. Am. Coll. Cardiol.* 20:1465–1473; Bowerman et al. (1991) *Cathet. Cardiovasc. Diagn.* 24:248–251; Moris et al. (1996) *Am. Heart. J.* 131:834–836; Schomig et al. (1994) *J. Am. Coll. Cardiol.* 23:1053–1060; Gordon et al. (1993) *J. Am. Coll. Cardiol.* 21:1166–1174; and Baim et al. (1993) *Am. J. Cardiol.* 71:364–366. These publications include descriptions of follow-up angioplasty and atherectomy as possible treatments for restenosis.

Atherectomy catheters having ultrasonic imaging transducers are descirbed in U.S. Pat. Nos. 5,000,185 and 5,100,424. Rotary ablation catheters having selectively expandable burr components are described in U.S. Pat. Nos. 5,217,474 and 5,308,354. A catheter carrying an expandable filter is described in U.S. Pat. No. 4,723,549.

Thrombectomy and atherectomy catheters having rotating brush and filament structures are described in U.S. Pat. Nos.

5,578,018; 5,535,756; 5,427,115; 5,370,653; 5,009,659; and 4,850,957; WO 95/29626; DE 39 21 071 C2; and Netherlands 9400027.

Representative atherectomy catheters are described in U.S. Pat. Nos. 4,273,128; 4,445,509; 4,653,496; 4,696,667; 4,706,671; 4,728,319; 4,732,154; 4,762,130; 4,790,812; 4,819,634; 4,842,579; 4,857,045; 4,857,046; 4,867,156; 4,883,458; 4,886,061; 4,890,611; 4,894,051; 4,895,560; 4,926,858; 4,966,604; 4,979,939; 4,979,951; 5,011,488; 5,011,489; 5,011,490; 5,041,082; 5,047,040; 5,071,424; 5,078,723; 5,085,662; 5,087,265; 5,116,352; 5,135,483; 5,154,724; 5,158,564; 5,160,342; 5,176,693; 5,192,291; 5,195,954; 5,196,024; 5,209,749; 5,224,945; 5,234,451; 5,269,751; 5,314,438; 5,318,576; 5,320,634; 5,334,211; 5,356,418; 5,360,432; 5,376,100; 5,402,790; 5,443,443; 5,490,859; 5,527,326; 5,540,707; 5,556,405; 5,556,408; and 5,554,163.

The disclosures of these patent are incorporated herein by reference in their entirety.

SUMMARY OF THE INVENTION

The present invention provides apparatus and methods for removing stenotic material from within previously stented regions of a patient's vasculature. The present invention is particularly intended for treating regions of restenosis within a stent which result from accumulation of cellular, thrombotic, and other material over the weeks and months following an initially successful stent implant. The present invention will also be useful for treating relatively rapid thrombus formation which may sometimes occur during the hours and days following a stent placement procedure.

Methods according to the present invention comprise operating a stenotic material removal mechanism within a blood vessel, typically a coronary artery or other artery, which has become restenosed or otherwise occluded following the initial stent placement, and sensing the proximity or contact between the stenotic material removal mechanism and the stent within the arterial wall so that the occluded vessel can be effectively recanalized without damaging the stent. The sensing means for sensing the proximity or contact between the stenotic material removal mechanism and the stent may be used to indicate an unsafe condition that might lead to stent damage, in response to which, the stenotic material removal mechanism may be manually or automatically deactivated. Alternatively or additionally, the sensing means may be used to indicate an appropriate endpoint for the stenotic material removal process.

According to this second aspect, the indication of the proximity or contact between the stenotic material removal mechanism and the stent provided by the sensing means may be used as feedback for controlling the stenotic material removal process in the following ways: When used in conjunction with a directional stenotic material removal mechanism, the sensing means may be used to guide the directional stenotic material removal mechanism either to remove stenotic material from selected portions of the interior of the stent or to remove stenotic material uniformly from the entire inner periphery of the stent. When used in conjunction with a controllable-depth stenotic material removal mechanism, the indication from the sensing means may be used as feedback to manually or automatically control the depth of stenotic material removal, preferably to remove stenotic material uniformly from the entire inner periphery of the stent. When used in conjunction with a controllable-width or diameter stenotic material removal mechanism, the indication from the sensing means may be used as feedback to manually or automatically control the width or diameter of the blood flow channel created within the stent. In certain embodiments of the method, the feedback from the sensing means may be used to control a combination of the directionality and the depth or diameter of the stenotic material removal process either to remove stenotic material from selected portions of the interior of the stent or to remove stenotic material uniformly from the entire inner periphery of the stent.

In a preferred aspect of the method of the present invention, a catheter carrying the stenotic material removal mechanism is positioned on one side of the restenosed stented region. The stenotic material removal mechanism is advanced from the catheter and positioned across the stenosis within the stent. The stenotic material removal mechanism is then expanded within the stenosis. The expansion may occur passively, as with a resilient stenotic material removal mechanism having one or more resilient members, such as one or more wire-shaped cutting blades, which are released from a tubular sheath and allowed to expand. Otherwise, the expansion may occur actively and controllably, such as with a stenotic material removal mechanism having one or more wire-shaped cutting blades which are actively and controllably extended outward to increase the width or diameter of the stenotic material removal mechanism, or such as a stenotic material removal mechanism having a cutter within a housing and an inflatable balloon located on one side of the housing which is inflated to increase the width or diameter of the stenotic material removal mechanism. The stenotic material removal mechanism is then activated for removing the stenotic material from within the stent. This is typically done by rotating and/or translating the entire stenotic material removal mechanism or a component of it within the stenosis. Medications, chemicals, ionizing radiation or energy, such as electrical, magnetic, ultrasonic, hydraulic, pulsed hydraulic, laser or thermal energy may be applied to assist in removal of the stenotic material and/or for denaturing the remaining tissue to discourage further restenosis at the treatment site. A sensing means which is located on or adjacent to the stenotic material removal mechanism monitors the proximity or contact between the stenotic material removal mechanism and the stent. When the stenotic material removal mechanism has approached close enough to the stent to indicate effective recanalization of the stenosis, the stenotic material removal mechanism is deactivated. In this way, the sensing means provides an interaction between the stenotic material removal mechanism and the stented vessel to achieve effective recanalization of the stenosis without damaging or dislodging the stent within the vessel wall.

In an alternative aspect of the method of the present invention, the catheter carrying the stenotic material removal mechanism is positioned on one side of the restenosed stented region. The stenotic material removal mechanism is extended from the catheter and advanced part-way into the stenosis within the stent. The stenotic material removal mechanism is then expanded within the stenosis, either passively or actively and controllably as described above, to increase the width or diameter of the stenotic material removal mechanism. The stenotic material removal mechanism is then activated for removing the stenotic material from within a portion of the stent. This may be done by rotating and/or translating the entire stenotic material removal mechanism or a component of it within the stenosis. Medications, chemicals, ionizing radiation or energy, such as electrical, magnetic, ultrasonic, hydraulic, pulsed hydraulic, laser or thermal energy may be applied to assist in removal of the stenotic material and/or for denaturing the remaining tissue to discourage further restenosis at the treatment site. A sensing means which is located on or adjacent to the stenotic material removal mechanism monitors the proximity or contact between the stenotic material removal mechanism and the stent. When the stenotic material removal mechanism has approached close enough to the stent to indicate effective recanalization of that portion of the stenosis, the stenotic material removal mechanism is advanced farther into the stenosis. The stenotic material removal mechanism may be deactivated and advanced stepwise into the stenosis by contracting or compressing the stenotic material removal mechanism, advancing it a short distance and expanding it again in a new portion of the stent. Otherwise, the stenotic material removal mechanism may be advanced continuously, relying on either the resiliency of the stenotic material removal mechanism or active control for adjusting the width or diameter of the stenotic material removal mechanism as it advances. When the sensing means indicates that the new portion of the stent has been effectively recanalized, the stenotic material removal mechanism is advanced again along the stenosis until the entire stented region has been recanalized.

Alternatively, the stenotic material removal mechanism may be extended from the catheter and advanced all the way across the stenosis in a contracted or compressed state. The stenotic material removal mechanism is then expanded within the far end of the stenosis or within the vessel beyond the stenosis, either passively or actively and controllably as described above, to increase the width or diameter of the stenotic material removal mechanism. The stenotic material removal mechanism is then activated for removing the stenotic material while withdrawing the stenotic material removal mechanism toward the catheter to advance it through the stenosis in either a step-wise or continuous fashion. Medications, chemicals, ionizing radiation or energy, such as electrical, magnetic, ultrasonic, hydraulic, pulsed hydraulic, laser or thermal energy may be applied to assist in removal of the stenotic material and/or for denaturing the remaining tissue to discourage further restenosis at the treatment site. The sensing means which is used to monitor the proximity or contact between the stenotic material removal mechanism and the stent in order to control the diameter and/or the rate of advancement of the stenotic material removal mechanism for effective recanalization of the stenosis within the stent.

The methods of the present invention may include providing a sensing means in the form of one or more open, exposed electrodes which are located on or adjacent to the stenotic material removal mechanism. A direct or alternating current reference voltage is applied to a unipolar electrode or applied between two bipolar electrodes, and the current leakage of the electrode or electrodes is monitored. When one or more of the electrodes contacts the metallic stent, the leakage current increases indicating that the stenotic material has been removed down to the stent support members for effective recanalization of the stenosis within that portion of the stent. Alternatively, the methods of the present invention may include providing a sensing means in the form of two exposed or insulated bipolar electrodes which are located on or adjacent to the stenotic material removal mechanism. An alternating current reference voltage is applied between the bipolar electrodes, and the complex impedance between the electrodes is monitored. As the electrodes approach the metallic stent, the capacitive and inductive characteristics of the electrode circuit change, which can be detected as a change in the complex impedance between the electrodes. When the complex impedance between the electrodes has changed a sufficient amount to indicate effective recanalization of the stenosis within that portion of the stent, the stenotic material removal mechanism may be deactivated or advanced along the stenosis as appropriate. The sensing means can be used to control or guide the stenotic material removal mechanism to remove the stenotic material to within a predetermined thickness of the stent support members or the stenotic material can be removed all the way down to the stent support members without fear of damaging the stent. If exposed electrodes are used in this method, monitoring the complex impedance between the electrodes will indicate when the stenotic material removal mechanism is approaching the metallic stent, then when one or more of the electrodes contacts the metallic stent, it will ground to the stent which can be detected as an extreme change in the complex impedance or as a rise in the leakage current. Thus, the sensing means can be used to separately indicate proximity and contact between the stenotic material removal mechanism and the stent. The sensing means can operate with very low voltage and current that will not create any adverse physiological effects on the vascular wall or the tissues and nerve pathways of the heart.

In embodiments where the stenotic material removal mechanism uses direct or alternating current electrical energy to assist in removal of the stenotic material and/or for denaturing the remaining tissue to discourage further restenosis at the treatment site, for example by heating or by radio frequency ablation, the heating or ablation electrodes can serve double duty as the sensing means electrodes for monitoring proximity or contact with the metallic stent.

Other types of proximity sensors sensitive to the metallic stent may be used in place of those described. Alternatively, optical or ultrasonic sensors may be used in place of the electronic detectors described for detection of both metallic and nonmetallic stents. For example, a nonimaging, A mode ultrasonic transducer can be used to detect both metallic and nonmetallic stents and to measure their depth within the arterial wall based on echoes caused by the difference in acoustic impedance between the stent material and the arterial tissue or stenosis.

The methods of the present invention will optionally further comprise collecting and withdrawing the removed stenotic material from the blood vessel. Collection and withdrawal of the removed stenotic material may be accomplished using the same catheter or catheter assembly which carries the stenotic material removal mechanism, typically by aspiration, entrapment, filtering or some combination thereof. It will be appreciated that various catheter assemblies can be put together using coaxially arranged components which may be introduced through a single vascular access point, such as a femoral or brachial artery. Alternatively, collection and withdrawal can be accomplished using separate collection apparatus, such as a catheter or catheter assembly, which is introduced through a separate access point. In some instances, it may be desirable to partially or totally isolate the stented region from circulation during recanalization. For example, embolic filters or occlusion balloons may be placed upstream and downstream of the treatment site. Alternatively or additionally, the methods of the present invention may optionally further comprise comminution of the removed stenotic material into microscopic particles that will not cause embolization downstream of the treatment site.

The methods of the present invention will also optionally comprise the use of introducer means, such as introducer needles, guidewires and/or introducer sheaths for introducing the catheter or catheter system into the vascular system and guide means, such as steerable guidewires and selective and/or subselective guiding or delivery catheters for guiding and advancing the catheter or catheter system through the vasculature to the treatment site and supporting it during the treatment. The selective and subselective guiding or delivery catheters may also serve the functions of aspiration, collection and withdrawal of the removed stenotic material, as well as for infusion of therapeutic substances.

Apparatus according to the present invention include catheters, catheter systems, and catheter kits which are specially intended and adapted for performing the methods described above. In particular, the apparatus are designed to afford percutaneous intravascular placement of a catheter carrying a stenotic material removal mechanism for removing stenotic material from within a previously stented region of the vasculature and a sensing means for sensing when the stenotic material removal mechanism is approaching or contacting the stent within the vascular wall. This inventive combination facilitates the effective recanalization of previously placed vascular stents that have become restenosed without risking damaging the stent. To that end, catheter systems according to the present invention may comprise an inner catheter shaft having a proximal end and a distal end. The stenotic material removal mechanism is disposed near the distal end of the inner catheter shaft. The inner catheter shaft will preferably include a guidewire lumen for introduction of the catheter system over a steerable guidewire. The inner catheter shaft may have additional lumens or actuating mechanisms associated with the stenotic material removal mechanism. Various embodiments of the stenotic material removal mechanism will be more fully described below. In embodiments where the stenotic material removal mechanism comprises resilient members which are radially compressible, the catheter system may also include a tubular sheath which serves to maintain the stenotic material removal mechanism in a compressed state as it is maneuvered to, and potentially across, the stenosis. The catheter system will usually further include an outer catheter tube having a proximal end, a distal end and an inner lumen. The outer catheter tube will usually have an aspiration port near its proximal end so that dislodged stenotic material can be aspirated from the vasculature. The outer catheter tube may optionally have selective or subselective curves formed near the distal end of the catheter tube for directing and maneuvering the catheter system through the vasculature to the site of the stenosis. In addition, an outer guiding catheter, for example a coronary guiding catheter, may be used for guiding the catheter system into the desired part of the vasculature and supporting it during the treatment.

The stenotic material removal mechanism which is disposed near the distal end of the inner catheter shaft may take one of several possible forms. In a first illustrative embodiment of the apparatus, the stenotic material removal mechanism is in the form of a cutting head having a plurality of longitudinally oriented cutting blades arranged radially about the central axis of the inner catheter. In a second illustrative embodiment of the apparatus, the stenotic material removal mechanism is in the form of a cutting head having a plurality of helically configured cutting blades arranged radially about the central axis of the inner catheter. In these first and second illustrative embodiments, each of the cutting blades is preferably shaped like a flattened wire with one or both lateral edges of the wire sharpened into a cutting edge. The wire-shaped cutting blades are resilient so that they can expand radially outward from the central axis of the inner catheter. Preferably, the wire-shaped cutting blades maintain an approximately parallel orientation to one another as they expand and contract in the radial direction so that the overall configuration of the cutting head is roughly cylindrical. The cutting head can be passively expandable, in which case the resilient wire-shaped cutting blades are treated by coldworking or heat treatment to have an elastic memory that predisposes them to expand outward when they are released from the radial constraint of the tubular sheath. Alternatively, the cutting head can be configured to be actively and controllably expandable. In this case, the resilient wire-shaped cutting blades are attached on their proximal ends to the inner catheter shaft and on their distal ends to an inner actuating member which is coaxially slidably with respect to the inner catheter shaft. When the inner actuating member is moved proximally with respect to the inner catheter shaft, the resilient wire-shaped cutting blades expand radially outward from the central axis of the inner catheter, and when the inner actuating member is moved distally with respect to the inner catheter shaft, the resilient wire-shaped cutting blades contract radially inward toward the central axis of the inner catheter. The resilient wire-shaped cutting blades may be treated by coldworking or heat treatment to have an elastic memory so that they are biased toward the contracted position, the expanded position or an intermediate position, each alternative having various advantages. The inner actuating member may be tubular, such as a polymer tube, a hollow flexible cable or a flexible metallic tube, so that the guidewire lumen can pass coaxially through the inner actuating member. Alternatively, the inner actuating member may be a thin wire which runs parallel to and alongside the guidewire lumen.

The stenotic material removal mechanism is operated by rotating the cutting head to remove the stenotic material from within the stent by the cutting action of the longitudinally oriented cutting blades. The rotating action of the blades may be accompanied by axially advancing or withdrawing the cutting head through the stenosis and/or by expanding the width or diameter of the cutting head. In accordance with the methods described above, one or more of the longitudinally oriented cutting blades includes a sensing means for sensing the proximity or contact between the cutting blades and the stent. The sensing means may be in the form of one or more electrode wires which are positioned on the cutting blades. When the sensing means detects sufficient proximity or contact between the cutting blades and the stent to indicate effective recanalization of the stenosis, the cutting head is deactivated and withdrawn from the stented vessel.

Additionally or alternatively, energy, such as electrical, ultrasonic or thermal energy may be applied through the cutting blades to assist in removal of the stenotic material and/or for denaturing the remaining tissue to discourage further restenosis at the treatment site. In this case, electrodes used for heating or ablation can serve double duty as the sensing means electrodes for monitoring proximity or contact with the stent.

In a third illustrative embodiment of the apparatus, the stenotic material removal mechanism is in the form of a blade which is extendible and retractable from within a cavity or lumen located near the distal end of the inner catheter. The blade is actuated to extend radially from the inner catheter by advancing an actuating member which extends through an inner lumen of the catheter to an advancement knob located near the proximal end of the inner catheter. Preferably, the blade maintains an approximately parallel orientation to the inner catheter as it extends and retracts in the radial direction. The stenotic material removal mechanism may operate by cutting action, in which case the blade is preferably shaped like a flattened wire with one or both lateral edges of the wire sharpened into a cutting edge, or it may operate by application of electrical or thermal energy, in which case the blade may be flat, round or any convenient shape.

The stenotic material removal mechanism is operated by advancing the actuating member to extend the blade radially from the inner catheter, then rotating the catheter about its longitudinal axis to remove the stenotic material from within the stent. The rotating action of the blades may be accompanied by axially advancing or withdrawing the inner catheter through the stenosis. A sensing means for sensing the proximity or contact between the blade and the stent is positioned on the blade of the catheter. The sensing means may be in the form of one or more electrode wires which are positioned on the cutting blade. If the stenotic material removal mechanism operates by electrical or thermal heating or ablation, the heating or ablation electrodes can also serve as the sensing means electrodes for monitoring proximity or contact with the stent. When the sensing means detects sufficient proximity or contact between the blade and the stent to indicate effective recanalization of the stenosis, the cutting blade is deactivated and withdrawn from the stented vessel.

In a fourth illustrative embodiment of the apparatus, the stenotic material removal mechanism has a cutter positioned within a housing. The housing has a side aperture which exposes the cutter and an inflatable balloon located on the back of the housing opposite the side aperture. The balloon can be inflated to increase the width or diameter of the stenotic material removal mechanism and thereby to control the depth of cut and the diameter of the blood flow channel created. The cutter may be a cup-shaped rotating blade, a rotating linear or helical blade, a rotating abrasive burr or a reciprocating or axially movable cutting blade. Additionally or alternatively, medications, chemicals, ionizing radiation or energy, such as electrical, magnetic, ultrasonic, hydraulic, pulsed hydraulic, laser or thermal energy may be applied through the cutter to assist in removal of the stenotic material and/or for denaturing the remaining tissue to discourage further restenosis at the treatment site.

The stenotic material removal mechanism is positioned by advancing the inner catheter so that the side aperture of the housing is situated across the stenosis within the stent and inflating the balloon to press the side aperture against the stenotic material. Then, the cutter is actuated by rotating and/or by axially advancing the cutter within the housing to remove stenotic material from within the stent. A sensing means for sensing the proximity or contact between the stenotic material removal mechanism and the stent is positioned on the cutter and/or the housing of the catheter. Again, the sensing means may be in the form of one or more electrode wires which are positioned on the cutter and/or the housing. If the stenotic material removal mechanism operates by electrical or thermal heating or ablation, the heating or ablation electrodes can also serve as the sensing means electrodes for monitoring proximity or contact with the stent. When the sensing means detects sufficient proximity or contact between the cutter and the stent to indicate the desired depth of cut, the cutter is deactivated and withdrawn or directed to another part of the stenosis within the stented portion of the vessel.

In a fifth illustrative embodiment of the apparatus, the stenotic material removal mechanism has a rotating cutting head attached to a hollow drive cable which is coaxially and rotatably positioned over a guidewire. The rotating cutting head is typically spherical or ovoid in shape and has cutting blades, teeth or abrasive particles on its exterior surface. Optionally, the inner catheter or guidewire may have a bend or a steering mechanism close to its distal end for directing the cutting head against the stenotic material within the stent. Alternatively or additionally, the cutting head may also have control means for adjusting the outer diameter of the cutting head. A sensing means for sensing the proximity or contact between the cutting head and the stent is positioned on the cutting head. The sensing means may be in the form of one or more electrodes which are positioned on the cutting head.

The stenotic material removal mechanism is operated by advancing the inner catheter so that the cutting head is positioned within the stenosis, then rotating the drive cable and the cutting head to remove stenotic material from within the stent. The rotating action of the cutting head may be accompanied by axially advancing or withdrawing the cutting head through the stenosis. The cutting blades, teeth or abrasive particles on the exterior surface of the cutting head comminute or pulverize the stenotic material into fine particles that will not cause embolization downstream of the treatment site. The optional bend or steering mechanism of the inner catheter or guidewire may be used for directing the cutting head against the stenotic material within the stent. Alternatively, the control means may be used for adjusting the diameter of the cutting head to achieve effective recanalization of the stented artery. When the sensing means indicates sufficient proximity or contact between the cutting head and the stent, the cutting head is deactivated and withdrawn or directed to another part of the stenosis within the stented portion of the vessel.

Each embodiment of the apparatus of the present invention will also include a monitoring means which couples to the sensor means of the catheter system through a connection fitting at the proximal end of the inner catheter. In one preferred embodiment, the monitoring means includes a voltage source that generates a direct or alternating current reference voltage which is applied to a unipolar electrode or applied between two bipolar electrodes positioned on the stenotic material removal mechanism, and an electrical monitor for monitoring the electrical conditions at the sensor electrode or electrodes. The electrical monitor may monitor the current leakage at the unipolar or bipolar sensor electrode to detect contact between the sensor electrode and a metallic stent and/or monitor the complex impedance across bipolar electrodes to detect proximity between the sensor electrodes and a metallic stent. The monitoring means may optionally include control means for deactivating the stenotic material removal mechanism when an unsafe condition that might lead to stent damage is detected or when the sensing means indicates an appropriate endpoint for the stenotic material removal process has been reached.

In an alternative embodiment, the monitoring means may be an optical sensor that includes an optical fiber which transmits a reference beam to a distal end of the catheter and directs it at the inner surface of the vessel close to the stenotic material removal mechanism. A photodetector detects the intensity and/or the wavelength of the light reflected back from the inner surface of the vessel through the optical fiber. A difference in reflectivity between the tissue of the vessel wall and the stent material allows the photodetector to detect proximity and/or contact between the stenotic material removal mechanism and the stent. In another alternative embodiment, the monitoring means may be a nonimaging, A mode ultrasonic scanner which generates a pulsed ultrasonic signal in a transducer mounted on or near the stenotic material removal mechanism. Differences in the acoustic impedance between the stent material and the arterial tissue or stenosis will cause echoes of the ultrasonic signal back to the transducer. The A mode ultrasonic scanner analyzes the amplitude and timing of the echoes detected by the ultrasonic transducer to measure the depth of the stent within the vessel wall. These two alternative embodiments of the monitoring means are useful for detection of both metallic and nonmetallic stents.

Preferably, each embodiment of the apparatus of the present invention will also include a motor drive unit which attaches at the proximal end of the catheter system. The motor drive unit houses a drive motor which is mechanically coupled to the inner catheter or the drive cable of the various embodiments to rotate and/or axially translate the stenotic material removal mechanism. For use with the first four embodiments of the apparatus described above, the drive motor is preferably a motor or gear motor which operates at relatively low speed for rotating the various cutters at a speed from 500 to 2000 rpm. For use with the fifth embodiment of the apparatus described above, the drive motor is preferably a high speed motor which rotates the cutting head at a speed from 2000 to 150000 rpm for effective comminution of the stenotic material. Alternatively, the stenotic material removal mechanism may be operated by hand.

Optionally, the apparatus of the present invention may further comprise means for collecting and withdrawing the removed stenotic material from the blood vessel. The means for collection and withdrawal of the removed stenotic material may include an irrigation and/or aspiration apparatus attached respectively to the inner and outer catheters of the catheter assembly. Additionally, embolic filters or occlusion balloons may be included in the catheter system for placement upstream and/or downstream of the treatment site. An embolic filters and other stenotic material capture means are described for use in conjunction and/or in a combined apparatus with the stenotic material removal mechanism.

BRIEF DESCRIPTION OF THE DRAWINGS

FIG. 11 is a side view of the distal portion and the proximal portion of a third embodiment of the apparatus of the present invention having a stenotic material removal mechanism with an extendible and retractable blade shown in the retracted position.

FIG. 12 is a side view of the apparatus of FIG. 11 showing the stenotic material removal mechanism in the extended position.

FIG. 13 is a magnified cross section of the cutting blade of the apparatus of FIG. 11 showing the sensor electrodes.

FIG. 14 is a side view of the distal portion of a fourth embodiment of the apparatus of the present invention showing a directional stenotic material removal mechanism with the balloon in the inflated position.

FIG. 15 is a top view of the apparatus of FIG. 14.

DESCRIPTION OF THE PREFERRED EMBODIMENT

Figure 1:
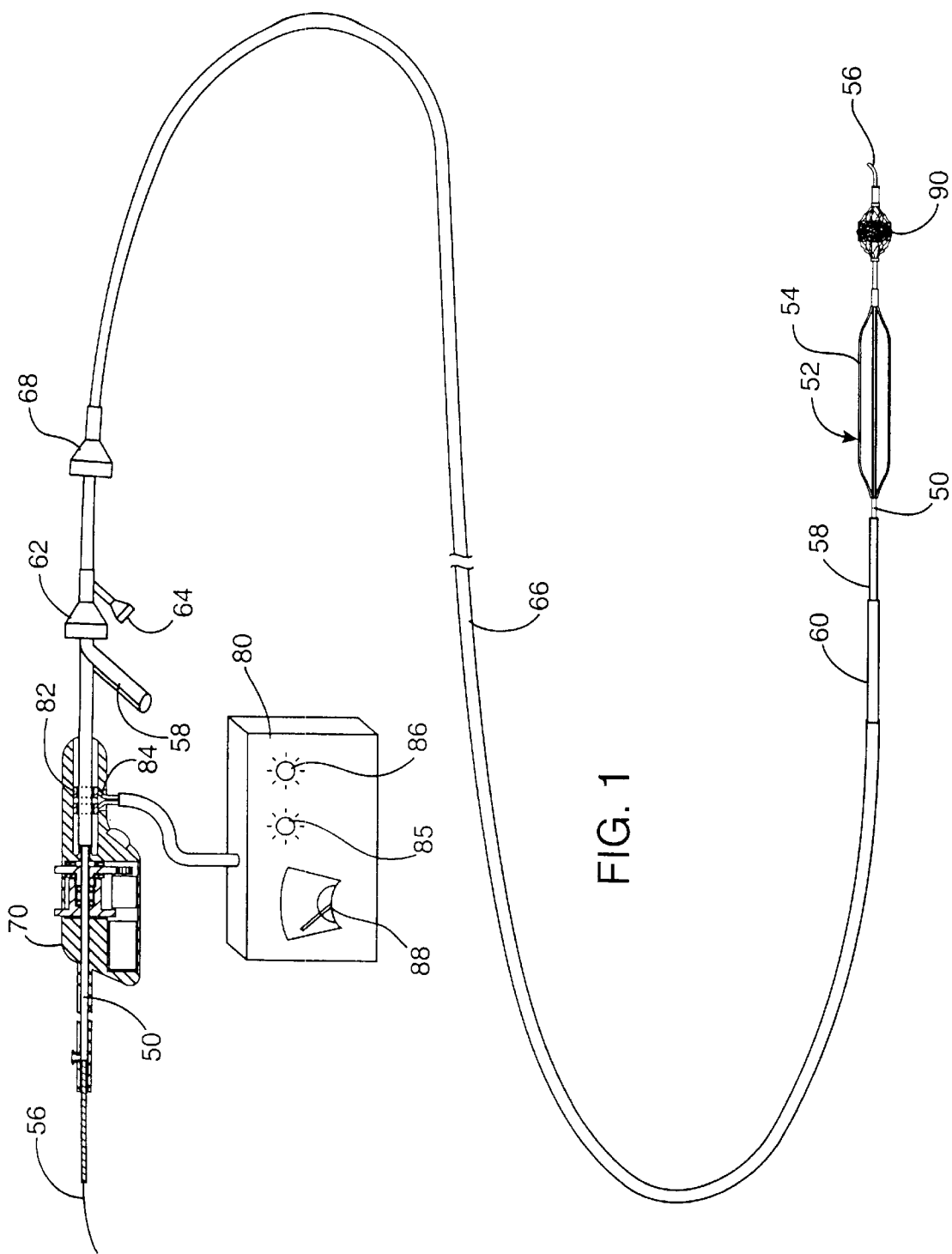
FIG. 1 is a generalized schematic diagram of the apparatus of the present invention showing the different components of the catheter system.
Figure 2:
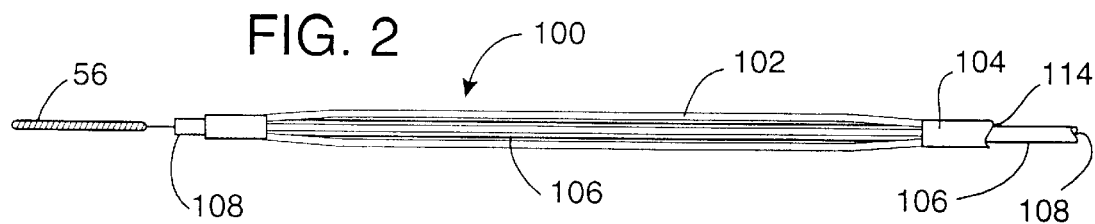
FIG. 2 is a side view of the distal portion of a first embodiment of the apparatus of the present invention having a stenotic material removal mechanism having with a plurality of longitudinally oriented cutting blades shown in the contracted position.

FIG. 1 is a generalized schematic diagram of the apparatus of the present invention. The apparatus comprises a catheter system designed to facilitate percutaneous removal of stenotic material from within a previously stented region of the vasculature without damaging or disrupting the implanted stent. In particular, the catheter system includes an inner catheter shaft 50 having a proximal end and a distal end, with a stenotic material removal mechanism 52 mounted near the distal end of the inner catheter shaft 50 and a sensing means 54 for sensing when the stenotic material removal mechanism 52 is approaching or contacting the stent within the vascular wall. The inner catheter shaft 50 will preferably include a guidewire lumen for introduction of the catheter system over a steerable guidewire 56. The inner catheter shaft 50 may have additional lumens or actuating mechanisms associated with the stenotic material removal mechanism 52. Various embodiments of the stenotic material removal mechanism 52 will be more fully described below. In embodiments where the stenotic material removal mechanism 52 comprises resilient members which are radially compressible, the catheter system may also include an optional tubular sheath 58 which serves to maintain the stenotic material removal mechanism 52 in a compressed state as it is maneuvered to, and potentially across, the stenosis. The tubular sheath 58 may be split or scored along its length so that is can be easily removed from around the inner catheter shaft 50 and discarded after the stenotic material removal mechanism 52 has been maneuvered into place.

The catheter system will usually further include an outer catheter tube 60 having a proximal end, a distal end and an inner lumen. The outer catheter tube will usually have a hemostasis valve 62 and an aspiration port 64 near its proximal end so that dislodged stenotic material can be aspirated from the vasculature. The outer catheter tube 60 may optionally have selective or subselective curves formed near the distal end of the outer catheter tube 60 for directing and maneuvering the catheter system through the vasculature to the site of the stenosis. In addition, an outer guiding catheter 66, for example a coronary guiding catheter, may be used for guiding the catheter system into the desired part of the vasculature and supporting it during the treatment. The guiding catheter 66 will have a Y-fitting with a hemostasis valve 68 connected at its proximal end.

Typically, the outer catheter 60 will have an overall length of approximately 60 cm to 120 cm, depending on the location of the vessel to be treated in the patient's body and the point of entry into the vasculature. For application in peripheral vessels or for application in the coronary arteries via a brachial artery insertion, the outer catheter 60 will typically have an overall length of approximately 60 cm to 90 cm. For application in the coronary arteries via a percutaneous femoral artery insertion, the outer catheter 60 will typically have an overall length of approximately 90 cm to 120 cm. The inner catheter 50 should have an overall length somewhat longer than the outer catheter 60 so that the stenotic material removal mechanism 52 can be extended out from the distal end of the outer catheter 60. The inner catheter 50 should therefore have an overall length of approximately 80 cm to 150 cm so that it can be extended 20 cm to 30 cm beyond the distal end of the outer catheter 60.

In a preferred embodiment, the catheter system includes a motor drive unit 70 which attaches at the proximal end of the inner catheter shaft 50. The motor drive unit 70 houses a drive motor 72 which is mechanically coupled to the inner catheter shaft 50 to rotate and/or axially translate the stenotic material removal mechanism 52 for removing stenotic material from within the stented vessel. The drive motor 72 may be a low speed motor or gear motor which operates at a speed from 500 to 2000 rpm or a high speed motor or a turbine which operates at a speed from 2000 to 150000 rpm. The operating speed of the drive motor 72 will be chosen according to the particular needs of the stenotic material removal mechanism 52, as will be discussed in more detail below. In alternative embodiments, the stenotic material removal mechanism 52 may be operated by hand.

The catheter system will also include a monitoring means 80 which couples to the sensor means 54 of the catheter system through a connection fitting 82 on the proximal end of the inner catheter shaft 50. Typically, the connection fitting 82 will electrically couple to the monitoring means 80 through a commutator 84 which is part of the motor drive unit 70. Alternatively, the monitoring means 80 may be miniaturized and incorporated as an integral part of the motor drive unit 70. The monitoring means 80 may include an audible alarm 85 and a visual alarm 86 to indicate contact between the stenotic material removal mechanism 52 and the stent and/or a visual gauge 88 of the proximity of the stenotic material removal mechanism 52 to the stent. The structure and function of the sensor means 54 and the monitoring means 80 will be discussed in further detail below.

Optionally, the catheter system may further include an embolic filter 90 which may be coaxially deployed over the same guidewire 56 as the rest of the catheter system. Alternatively, embolic filters and/or occlusion balloons may be deployed on separate catheters for placement upstream and/or downstream of the treatment site.

Figure 3:
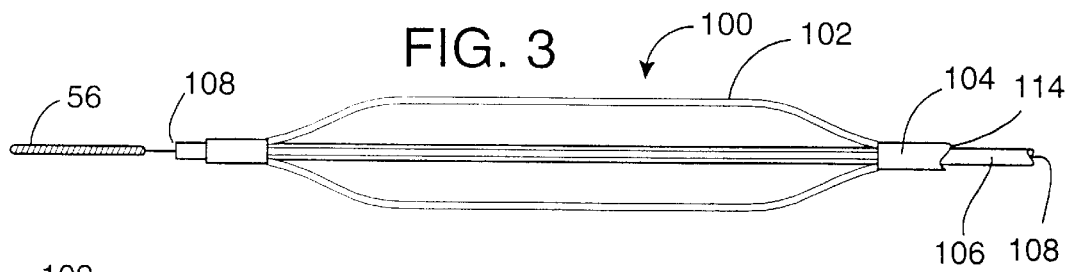
FIG. 3 is a side view of the apparatus of FIG. 2 showing the stenotic material removal mechanism in the expanded position.
Figure 4:
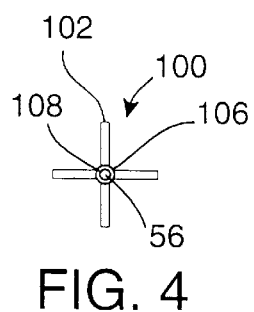
FIG. 4 is a distal end view of the apparatus of FIG. 2 with the stenotic material removal mechanism in the expanded position.

The stenotic material removal mechanism which is disposed near the distal end of the inner catheter shaft may take one of several possible forms. The distal portion of a first illustrative embodiment of an inner catheter according to the apparatus of the present invention is depicted in FIGS. 2–6. In this embodiment, the stenotic material removal mechanism is in the form of a cutting head 100 having a plurality of longitudinally oriented cutting blades 102 arranged radially about the central axis of the inner catheter shaft 104. The cutting head 100 is shown in a contracted position in FIG. 2 with the cutting blades 102 compressed closely around the central axis of the inner catheter shaft 104. FIG. 3 shows the cutting head 100 in an expanded position with the cutting blades 102 extending radially outward from the central axis of the inner catheter shaft 104. FIG. 4 shows a distal end view of the cutting head 100 in the expanded position. In variations of this embodiment, there may be two, three, four or more longitudinally oriented cutting blades 102. Each of the cutting blades 102 is preferably shaped like a flattened wire with one or both lateral edges 110, 112 of the wire sharpened into a cutting edge, as shown in the cross section of FIG. 6. The wire-shaped cutting blades 102 are resilient so that they can expand radially outward from the central axis of the inner catheter shaft 104. Preferably, the wire-shaped cutting blades 102 maintain an approximately parallel orientation to one another as they expand and contract in the radial direction so that the overall configuration of the cutting head 100 is roughly cylindrical. The cutting blades 102 are preferably made of a strong and resilient biocompatible material capable of holding a sharp cutting edge. Suitable materials for the cutting blades 102 include metals, such as stainless steel, titanium and nickel/titanium alloys, and cobalt alloys like Elgiloy and MP35. Composite constructions are also possible for the cutting blades 102.

The cutting head 100 can be passively expandable, in which case the resilient wire-shaped cutting blades 102 are treated by coldworking or heat treatment to have an elastic memory that predisposes them to expand outward when they are released from the radial constraint of the tubular sheath 58 which was shown in FIG. 1. Alternatively, the cutting head 100 can be configured to be actively and controllably expandable. In this case, the resilient wire-shaped cutting blades 102 are attached on their proximal ends to the inner catheter shaft 104 and on their distal ends to an inner actuating member 106 which is coaxially slidably with respect to the inner catheter shaft 104. When the inner actuating member 106 is moved proximally with respect to the inner catheter shaft 104, the cutting blades 102 expand radially outward from the central axis of the inner catheter shaft 104, and when the inner actuating member 106 is moved distally with respect to the inner catheter shaft 104, the cutting blades 102 contract radially inward toward the central axis of the inner catheter shaft 104. The cutting blades 102 may be treated by coldworking or heat treatment to have an elastic memory so that they are biased toward the contracted position so that the cutting head 100 will contract easily for advancing it across tight stenotic lesions, or toward a fully expanded position so that the cutting head 100 will be easy to deploy. Alternatively, the resilient wire-shaped cutting blades 102 may be treated so that they are biased toward an intermediate position which corresponds with a nominal expanded diameter. The inner actuating member 106 may be tubular, such as a polymer tube, a hollow flexible cable or a flexible metallic tube, so that a lumen 108 for a guidewire 56 can pass coaxially through the inner actuating member 106. Alternatively, the inner actuating member may be a thin wire which runs parallel to and alongside the guidewire lumen.

The inner catheter shaft 104 is a tubular structure with an inner lumen 114 for passing the guidewire 56 and, in some embodiments, the inner actuating member 106 through. The inner catheter shaft 104 may be a polymer tube, a braid reinforced polymer tube, a hollow flexible cable, such as a multifilar wound cable, or a flexible metallic tube. The inner catheter shaft 104 acts as a flexible drive shaft for transmitting rotation and torque from the drive motor 72 (FIG. 1) to the cutting head 100. The stenotic material removal mechanism is operated by rotating the cutting head 100 to remove the stenotic material from within the stent by the cutting action of the longitudinally oriented cutting blades 102. The rotating action of the blades 102 may be accompanied by axially advancing or withdrawing the cutting head 100 through the stenosis and/or by expanding the width or diameter of the cutting head 100. The cutting head 100 should be expandable over a range of approximately 2 mm to 5 mm for use in stented coronary arteries or as high as 6 mm for use in stented vein grafts and even larger for use in stented peripheral vessels and other stented body structures. The cutting head 100 should contract to as small a diameter as possible for passing through tightly stenotic lesions, preferably to a diameter smaller than 2 mm, more preferably to a diameter smaller than 1 mm. The effective cutting length of the cutting head 100 is preferably within the range of approximately 10 mm to 40 mm for use in stented coronary arteries and can be longer for use in stented peripheral vessels.

Figure 5:
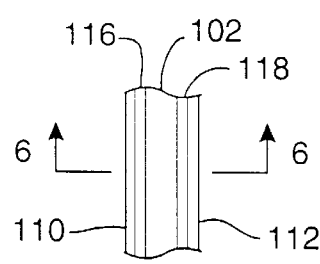
FIG. 5 is a magnified cutaway view of a cutting blade of the apparatus of FIG. 2 showing the sensor electrodes.
Figure 6:
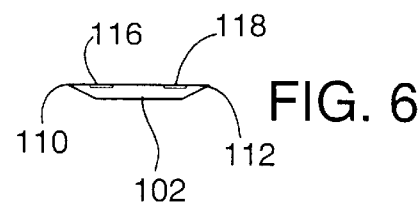
FIG. 6 is a cross section of the cutting blade of FIG. 5.

One or more, or all, of the longitudinally oriented cutting blades 102 includes a sensing means for sensing the proximity or contact between the cutting blades 102 and the stent. In this illustrative embodiment, the sensing means are provided in the form of one or more electrode wires 116, 118 which are positioned on the cutting blades, as best seen in FIGS. 5 and 6. The sensing electrodes 116, 118 may extend the full length of the cutting blades 102 or only a portion of it, or the sensing electrodes 116, 118 may be arranged to provide a plurality of sensing locations along the length of the cutting blades 102. In a first implementation of this embodiment, one or more open, exposed electrodes 116, 118 are located on the surface of the cutting blades 102. Alternatively, the cutting blades 102 themselves may serve as the sensor electrodes. A direct or alternating current reference voltage is applied to a unipolar electrode or applied between two bipolar electrodes, and the current leakage of the electrode or electrodes is monitored. When one or more of the electrodes 116, 118 contacts the metallic stent, the leakage current increases indicating that the stenotic material has been removed down to the stent support members for effective recanalization of the stenosis within that portion of the stent. A second implementation of this embodiment involves two capacitively coupled bipolar electrodes 116, 118 which are located on the surface of the cutting blades 102. An alternating current reference voltage is applied between the bipolar electrodes 116, 118, and the complex impedance between the electrodes is monitored. As the electrodes 116, 118 approach the metallic stent, the capacitive and inductive characteristics of the electrode circuit change, which can be detected as a change in the complex impedance between the electrodes. When the complex impedance between the electrodes has changed a sufficient amount to indicate effective recanalization of the stenosis within that portion of the stent, the stenotic material removal mechanism may be deactivated or advanced along the stenosis as appropriate. These two implementations can be combined by applying an alternating current reference voltage between two exposed bipolar electrodes 116, 118, and monitoring the complex impedance between the electrodes to indicate when the stenotic material removal mechanism is approaching the metallic stent, then when one or more of the electrodes contacts the metallic stent, it will ground to the stent which can be detected as an extreme change in the complex impedance or as a rise in the leakage current. Thus, the sensing means can be used to separately indicate proximity and contact between the cutting blades 102 and the stent. The sensing means can operate with very low voltage and current that will not create any adverse physiological effects on the vascular wall or the tissues and nerve pathways of the heart.

Figure 7:
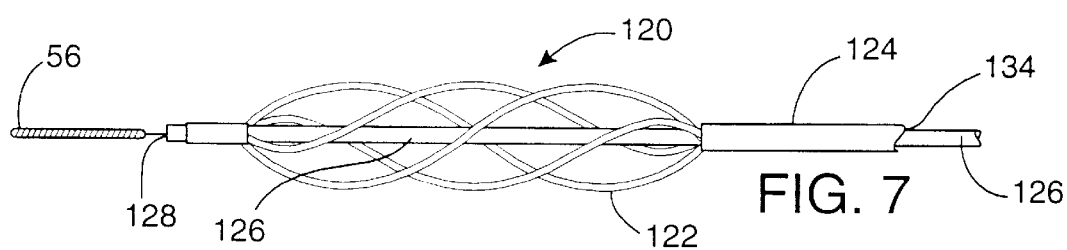
FIG. 7 is a side view of the distal portion of a second embodiment of the apparatus of the present invention having a stenotic material removal mechanism having with a plurality of helically configured cutting blades shown in the expanded position.
Figure 8:
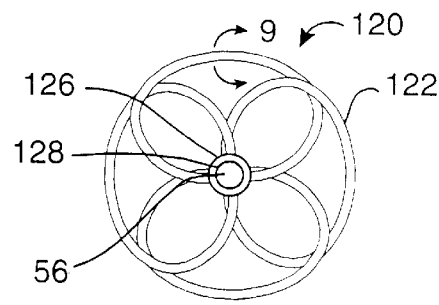
FIG. 8 is an enlarged distal end view of the apparatus of FIG. 7 with the stenotic material removal mechanism in the expanded position.

The distal portion of a second illustrative embodiment of an inner catheter according to the apparatus of the present invention is depicted in FIGS. 7–10. In this embodiment, the stenotic material removal mechanism is in the form of a cutting head 120 having a plurality of helically configured cutting blades 122 arranged radially about the central axis of the inner catheter shaft 124, as shown in FIG. 7. FIG. 8 shows an enlarged distal end view of the cutting head 120 in the expanded position. In variations of this embodiment, there may be two, three, four or more helically configured cutting blades 122. Preferably, each of the cutting blades 122 is shaped like a flattened wire with one or both lateral edges 130, 132 of the wire sharpened into a cutting edge, as shown in the cross section of FIG. 10. Preferably, the helically configured cutting blades 122 maintain an approximately parallel orientation to one another as they expand and contract in the radial direction so that the overall configuration of the cutting head 120 is roughly cylindrical. The cutting blades 122 are made of a strong and resilient biocompatible material capable of holding a sharp cutting edge, such as stainless steel, titanium and nickel/titanium alloys, and cobalt alloys like Elgiloy and MP35, or a composite construction.

As with the first embodiment, the cutting head 120 can be passively expandable or actively and controllably expandable. In the latter case, the helically configured cutting blades 122 are attached on their proximal ends to the inner catheter shaft 124 and on their distal ends to an inner actuating member 126 which slides proximally and distally with respect to the inner catheter shaft 124 to expand and contract diameter of the cutting head 120, respectively. The cutting blades 122 may be treated by coldworking or heat treatment to have an elastic memory so that they are biased toward the contracted position, the expanded position or an intermediate position. The inner actuating member 126 may be tubular, such as a polymer tube, a hollow flexible cable or a flexible metallic tube, so that a lumen 128 for a guidewire 56 can pass coaxially through the inner actuating member 126. Alternatively, the inner actuating member may be a thin wire which runs parallel to and alongside the guidewire lumen.

The inner catheter shaft 124 is a tubular structure with an inner lumen 134 for passing the guidewire 56 and, in some cases, the inner actuating member 126 through. The inner catheter shaft 124 may be a polymer tube, a braid reinforced polymer tube, a hollow flexible cable, such as a multifilar wound cable, or a flexible metallic tube that serves as a flexible drive shaft for transmitting rotation and torque from the drive motor 72 (FIG. 1) to the cutting head 120. The stenotic material removal mechanism is operated by rotating the cutting head 120 to remove the stenotic material from within the stent by the cutting action of the helically configured cutting blades 122. The rotating action of the blades 122 may be accompanied by axially advancing or withdrawing the cutting head 120 through the stenosis and/or by expanding the width or diameter of the cutting head 120. The cutting head 120 should be expandable over a range of approximately 2 mm to 5 mm for use in stented coronary arteries or as high as 6 mm for use in stented vein grafts and even larger for use in stented peripheral vessels and other stented body structures. The cutting head 120 should contract to as small a diameter as possible for passing through tightly stenotic lesions, preferably to a diameter smaller than 2 mm, more preferably to a diameter smaller than 1 mm. The effective cutting length of the cutting head 120 is preferably within the range of approximately 10 mm to 40 mm for use in stented coronary arteries and can be longer for use in stented peripheral vessels.

Figure 9:
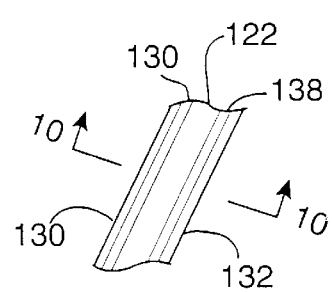
FIG. 9 is a magnified cutaway view of a cutting blade of the apparatus of FIG. 7 showing the sensor electrodes.
Figure 10:
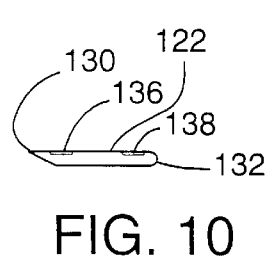
FIG. 10 is a cross section of the cutting blade of FIG. 9.

One or more, or all, of the helically configured cutting blades 122 includes a sensing means for sensing the proximity or contact between the cutting blades 122 and the stent. As shown in FIGS. 9 and 10, the sensing means may be in the form of one or more electrode wires 136, 138 which are positioned on the surface of the cutting blades 122. The sensing electrodes 136, 138 may extend the full length of the cutting blades 122 or only a portion of it, or the sensing electrodes 136, 138 may be arranged to provide a plurality of sensing locations along the length of the cutting blades 122. As in the first embodiment described above, the electrodes 136, 138 may be exposed or insulated and unipolar or bipolar. Alternatively, the cutting blades 122 themselves may serve as the sensor electrodes. Contact and/or proximity between the cutting blades 122 and the stent can be monitored by sensing the leakage current and/or the complex impedance of the sensor electrode circuit. When the sensing means detects sufficient proximity or contact between the cutting blades 122 and the stent to indicate effective recanalization of the stenosis within that portion of the stent, the cutting head 120 may be deactivated or advanced along the stenosis as appropriate.

The distal portion and the proximal portion of a third illustrative embodiment of an inner catheter according to the apparatus of the present invention is depicted in FIGS. 11–13. In this embodiment, the stenotic material removal mechanism is in the form of a blade 140 which is extendible and retractable from within a cavity 142 located near the distal end of the inner catheter shaft 144. The blade 140 is actuated to extend radially from the inner catheter shaft 144 by advancing an actuating member 146 which extends through an inner lumen 148 of the catheter to an advancement knob 152 which is located on a handle assembly 150 near the proximal end of the inner catheter shaft 144. FIG. 11 is a side view of the inner catheter with the blade 140 on the distal portion of the inner catheter shaft 144 and the advancement knob 152 on the proximal handle assembly 150 in the retracted position. FIG. 12 is a side view of the inner catheter with the blade 140 and the advancement knob 152 in the extended position. Preferably, the blade 140 maintains an approximately parallel orientation to the inner catheter shaft 144 as it extends and retracts in the radial direction. The blade 140 may be treated by coldworking or heat treatment to have an elastic memory so that it is biased toward the retracted position, in which case the blade 140 will be extended by a compression force applied to the actuating member 146 by the advancement knob 152 on the handle assembly 150. Alternatively, the blade 140 may be treated to be biased toward the extended position, in which case the blade 140 will be self-extending and will be retracted by a tensile force applied to the actuating member 146 by the advancement knob 152. Accordingly, the actuating member 146 may be a thin wire, a flexible cable, or a thin tensile filament.

The inner catheter shaft 144 is a tubular structure with an inner lumen 162 which extends to the distal end for passing a guidewire 56 through for directing the catheter into and across a stented region in an artery. The inner catheter shaft 144 may be a polymer tube, a braid reinforced polymer tube, a hollow flexible cable, such as a multifilar wound cable, or a flexible metallic tube. Preferably, the inner catheter shaft 144 has sufficient torsional rigidity to serve as a flexible drive shaft for transmitting rotation and torque from the proximal handle assembly 150 to the blade 140 on the distal end of the inner catheter shaft 144. The torque may be applied to the proximal handle assembly 150 manually by the operator or the proximal handle assembly 150 may include a drive motor 72, as in FIG. 1.

The stenotic material removal mechanism is operated by advancing the actuating member 146 to extend the blade 140 radially from the inner catheter shaft 144, then rotating the catheter shaft 144 about its longitudinal axis to remove the stenotic material from within the stent. The rotating action of the blade 140 may be accompanied by axially advancing or withdrawing the inner catheter through the stenosis. In one preferred embodiment, the stenotic material removal mechanism of the inner catheter operates by cutting action, in which case the blade 140 is preferably shaped like a flattened wire with one or both lateral edges 154, 156 of the wire sharpened into a cutting edge, as shown in the magnified cross section of the cutting blade in FIG. 13. The cutting blade 140 is made of a strong and resilient biocompatible material capable of holding a sharp cutting edge, such as stainless steel, titanium and nickel/titanium alloys, and cobalt alloys like Elgiloy and MP35, or a composite construction. The cutting blade 140 includes a sensing means for sensing the proximity or contact between the cutting blade 140 and the stent. As shown in FIG. 13, the sensing means may be in the form of one or more electrode wires 158, 160 which are positioned on the surface of the cutting blade 140. The electrodes 158, 160 may be exposed or insulated and unipolar or bipolar. Alternatively, the cutting blade 140 itself may serve as a unipolar sensor electrode. Contact and/or proximity between the cutting blade 140 and the stent can be monitored by sensing the leakage current and/or the complex impedance of the sensor electrode circuit. When the sensing means detects sufficient proximity or contact between the cutting blade 140 and the stent to indicate effective recanalization of the stenosis within that portion of the stent, the cutting head 120 may be deactivated or advanced along the stenosis as appropriate.

Additionally or alternatively, energy, such as electrical, ultrasonic or thermal energy may be applied through the blade 140 to assist in removal of the stenotic material and/or for denaturing the remaining tissue to discourage further restenosis at the treatment site. In this case, electrodes used for heating or ablation can also serve as the sensing means electrodes for monitoring proximity or contact with the stent. If the device relies principally on ablation as the stenotic material removal technique, the blade 140 need not be sharpened as shown, but may instead be flat, round or any convenient shape.

The distal portion of a fourth illustrative embodiment of an inner catheter according to the apparatus of the present invention is depicted in FIGS. 14–15. In this embodiment, the stenotic material removal mechanism 170 has a cutter 172 positioned within a housing 174. The housing 174 has a side aperture 176 which exposes the cutter 172 and an inflatable balloon 180 located on the back of the housing 174 opposite the side aperture 176. The balloon 180 can be inflated with fluid injected through a balloon lumen 182 to increase the width or diameter of the stenotic material removal mechanism 170 and thereby to control the depth of cut and the diameter of the blood flow channel created. The balloon 180 may be made of polyethylene, polyester, nylon or other polymeric materials. The cutter 172 may be a cup-shaped rotating blade, a rotating linear or helical blade, a rotating abrasive burr or an axially movable cutting blade, which is rotated and/or translated by a drive shaft 178 that extends proximally through a lumen 186 within the catheter shaft 184. Additionally or alternatively, medications, chemicals, ionizing radiation or energy, such as electrical, magnetic, ultrasonic, hydraulic, pulsed hydraulic, laser or thermal energy may be applied through the cutter 172 to assist in removal of the stenotic material and/or for denaturing the remaining tissue to discourage further restenosis at the treatment site.

The catheter shaft 184 is a tubular structure which includes the balloon lumen 182 and the drive shaft lumen 186. The catheter shaft 184 may be a polymer tube, a braid reinforced polymer tube, a hollow flexible cable, such as a multifilar wound cable, or a flexible metallic tube. Preferably, the catheter shaft 184 has sufficient torsional rigidity to rotate the housing 174 on the distal end of the catheter by rotating the proximal end of the catheter shaft 184. The drive shaft 178 may be a hollow tube with a guidewire lumen 190 which extends to the distal end for passing a guidewire 56 through for directing the catheter into and across a stented region in an artery. The drive shaft 178 may be a polymer tube, a braid reinforced polymer tube, a hollow flexible cable, such as a multifilar wound cable, or a flexible metallic tube. Alternatively, the drive shaft 178 may be a solid wire, in which case the guidewire lumen 190 could be a separate lumen within the catheter shaft 184.

In operation, the stenotic material removal mechanism 170 is positioned by advancing and rotating the inner catheter so that the side aperture 176 of the housing 174 is situated across the stenosis within the stent and inflating the balloon 180 to press the side aperture 176 against the stenotic material. Then, the cutter 172 is actuated by rotating and/or by axially advancing the cutter 172 within the housing 174 to remove stenotic material from within the stent. A sensing means 188, 188' for sensing the proximity or contact between the stenotic material removal mechanism 170 and the stent is positioned on the cutter 172 and/or the housing 174 of the catheter. Again, the sensing means 188, 188' may be in the form of one or more electrode wires which are positioned on the cutter 172 and/or the housing 174. If the stenotic material removal mechanism 170 operates by electrical or thermal heating or ablation, the heating or ablation electrodes can also serve as the sensing means electrodes for monitoring proximity or contact with the stent. When the sensing means detects sufficient proximity or contact between the cutter 172 and the stent to indicate the desired depth of cut, the cutter 172 is deactivated and withdrawn or directed to another part of the stenosis within the stented portion of the vessel.

Figure 16:
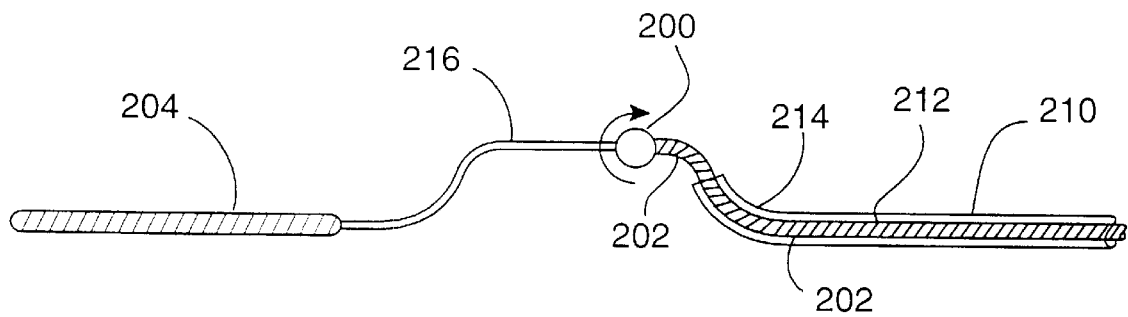
FIG. 16 is a side view of the distal portion and the proximal portion of a fifth embodiment of the apparatus of the present invention having an abrasive cutting head.
Figure 17:
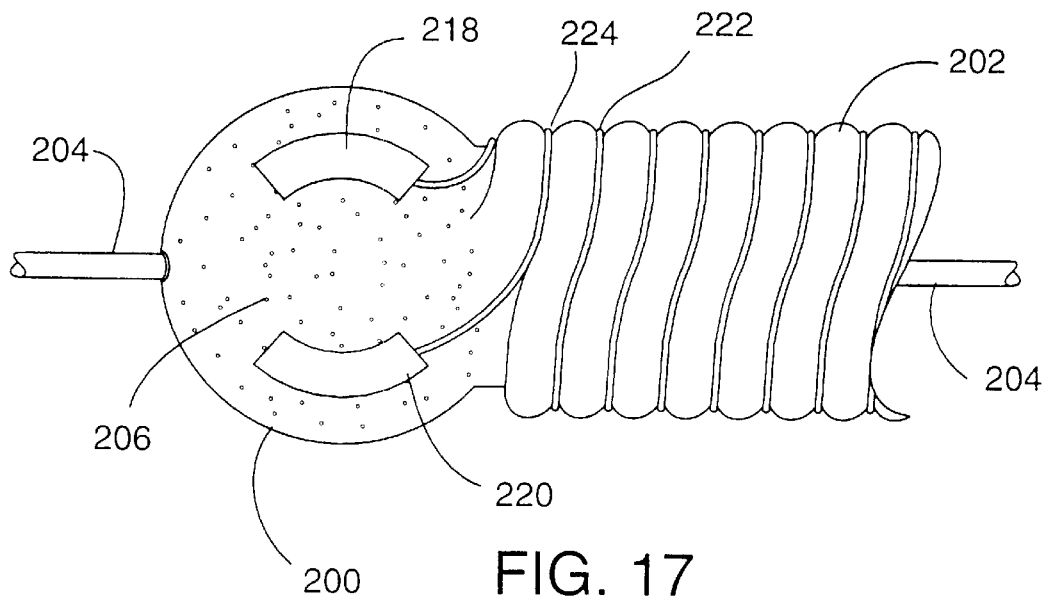
FIG. 17 is a magnified view of the cutting head of the apparatus of FIG. 16 showing the sensor electrodes.

The distal portion of a fifth illustrative embodiment of an inner catheter according to the apparatus of the present invention is depicted in FIGS. 16–17. In this embodiment, the stenotic material removal mechanism is rotatably and slidably received within an inner lumen 212 of the inner catheter shaft 210. The stenotic material removal mechanism has a rotating cutting head 200 attached to a hollow drive cable 202 which is coaxially and rotatably positioned over a guidewire 204. The rotating cutting head 200 is typically spherical or ovoid in shape and has cutting blades, teeth or abrasive particles 206 on its exterior surface. In one preferred embodiment, the cutting head 200 has minute diamond abrasive particles 206 embedded on its exterior surface. The hollow drive cable 202 is preferably a multifilar wound cable, but alternatively may be a polymer tube, a braid reinforced polymer tube, a hollow flexible cable or a flexible metallic tube. Optionally, the inner catheter shaft 210 and/or the guidewire 204 may have a bend 214, 216 or other steering mechanism close to its distal end for directing the cutting head 200 against the stenotic material within the stent. Alternatively or additionally, the cutting head 200 may also have control means for adjusting the outer diameter of the cutting head 200. Suitable cutting head diameter control means are described in U.S. Pat. Nos. 5,217,474 and 5,308,354, the specifications of which are hereby incorporated by reference in their entirety.

A sensing means for sensing the proximity or contact between the cutting head 200 and the stent is positioned on the cutting head 200. The sensing means may be in the form of one or more electrodes 218, 220 which are positioned on the cutting head 200. One or more electrode lead wires 222, 224 may be incorporated into the multifilar hollow drive cable 202. The electrodes 218, 220 may be exposed or insulated and unipolar or bipolar. Alternatively, the cutting head 200 itself may serve as a unipolar sensor electrode and the multifilar hollow drive cable 202 may serve as a single electrode lead wire.

The stenotic material removal mechanism is operated by advancing the inner catheter so that the cutting head 200 is positioned within the stenosis, then rotating the drive cable 202 and the cutting head 200 to remove stenotic material from within the stent. Preferably, the cutting head 200 is rotated with a high speed motor or turbine which rotates the cutting head at a speed from 2000 to 150000 rpm. The rotating action of the cutting head 200 may be accompanied by axially advancing or withdrawing the cutting head 200 through the stenosis. The cutting blades, teeth or abrasive particles 206 on the exterior surface of the cutting head 200 comminute, or pulverize, the stenotic material into fine particles that will not cause embolization downstream of the treatment site. The optional bend 214, 216 or steering mechanism of the inner catheter 210 or guidewire 204 may be used for directing the cutting head 200 against the stenotic material within the stent. Alternatively, the control means may be used for adjusting the diameter of the cutting head 200 to achieve effective recanalization of the stented artery. When the sensing means indicates sufficient proximity or contact between the cutting head 200 and the stent, the cutting head 200 is deactivated and withdrawn or advanced and directed to another part of the stenosis within the stented portion of the vessel.

The function of the monitoring means 80 of the catheter system, shown generically in FIG. 1, will be more fully appreciated in light of the foregoing descriptions of the various embodiments of the stenotic material removal mechanism and their related sensing means. In one preferred embodiment, the monitoring means includes a voltage source that generates a direct or alternating current reference voltage which is applied to a unipolar electrode or applied between two bipolar electrodes positioned on the stenotic material removal mechanism, and an electrical monitor for monitoring the electrical conditions at the sensor electrode or electrodes. The electrical monitor may monitor the current leakage at the unipolar or bipolar sensor electrode to detect contact between the sensor electrode and a metallic stent and/or monitor the complex impedance across bipolar electrodes to detect proximity between the sensor electrodes and a metallic stent. The monitoring means may optionally include control means for deactivating the stenotic material removal mechanism when an unsafe condition that might lead to stent damage is detected or when the sensing means indicates that an appropriate endpoint for the stenotic material removal process has been reached.

In cases where the sensing means provides separate sensing electrodes on the different blades of the stenotic material removal mechanism or where a plurality of sensing locations are provided along the length of the stenotic material removal mechanism, the monitoring means 80 can be designed to monitor each of the multiple electrodes or sensing locations simultaneously, or it can be designed to have an appropriate sampling rate for alternately monitoring each of the electrodes or sensing locations in sequence.

In an alternative embodiment, the monitoring means may be an optical sensor that includes an optical fiber which transmits a reference beam to a distal end of the catheter and directs it at the inner surface of the vessel close to the stenotic material removal mechanism. A photodetector detects the intensity and/or the wavelength of the light reflected back from the inner surface of the vessel through the optical fiber. A difference in reflectivity between the tissue of the vessel wall and the stent material allows the photodetector to detect proximity and/or contact between the stenotic material removal mechanism and the stent.

In another alternative embodiment, the monitoring means may be a nonimaging, A mode ultrasonic scanner which generates a pulsed ultrasonic signal in a transducer mounted on or near the stenotic material removal mechanism. Differences in the acoustic impedance between the stent material and the arterial tissue or stenosis will cause echoes of the ultrasonic signal back to the transducer. The A mode ultrasonic scanner analyzes the amplitude and timing of the echoes detected by the ultrasonic transducer to measure the depth of the stent within the vessel wall. These two alternative embodiments of the monitoring means are useful for detection of both metallic and nonmetallic stents. A nonimaging, A mode ultrasonic scanner of this type is much more economical than the imaging ultrasonic scanners which have been described in combination with various atherectomy devices. The high echogenicity of the stent material will give a reliable measure of the depth of the stent within the vessel wall without the need for expensive imaging equipment.

FIGS. 18, 19, 20 and 21 are a series of drawings illustrating the method of the present invention. The method is illustrated and described using the apparatus of FIG. 1 with the stenotic material removal mechanism of FIGS. 2–6 by way of example. This method may be applied using any of the various apparatus described above with minor modifications to the procedure. The catheter system of FIG. 1 is introduced into the patient's vascular system through a peripheral arterial access using the known techniques of an arterial cutdown, the Seldinger technique and/or an introducer sheath. The catheter system is maneuvered to the vicinity of a restenosed region within a previously stented region of the vasculature, for example within a coronary artery, using manipulations of the optional guiding catheter 66 and the outer catheter 60 of the catheter system. The inner catheter 50 carrying the stenotic material removal mechanism 52 is positioned on one side of the restenosed stented region and the steerable guidewire 56 is maneuvered across the stenosis.

Figure 18:
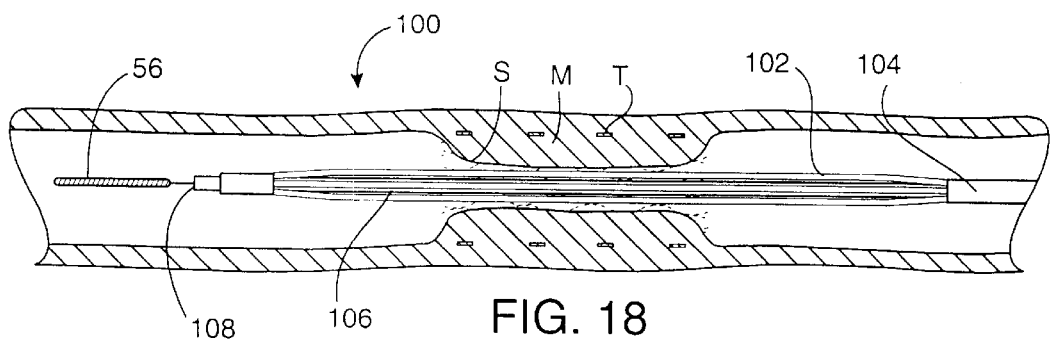
FIGS. 18, 19, 20 and 21 are a series of drawings illustrating the method of the present invention using the apparatus of FIG. 2.
Figure 19:
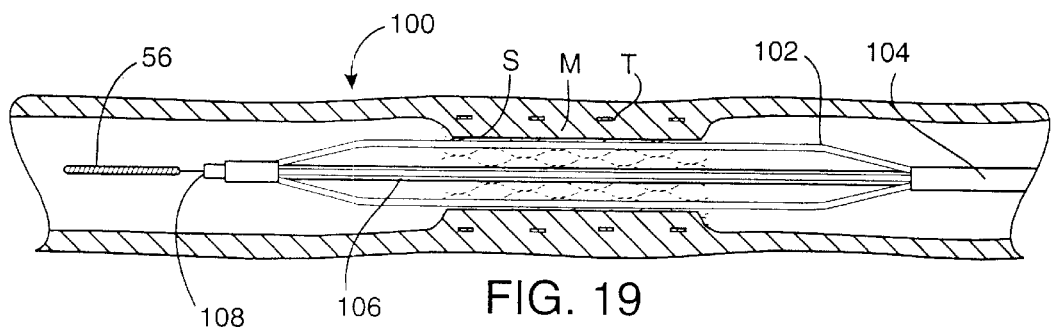
Figure 20:
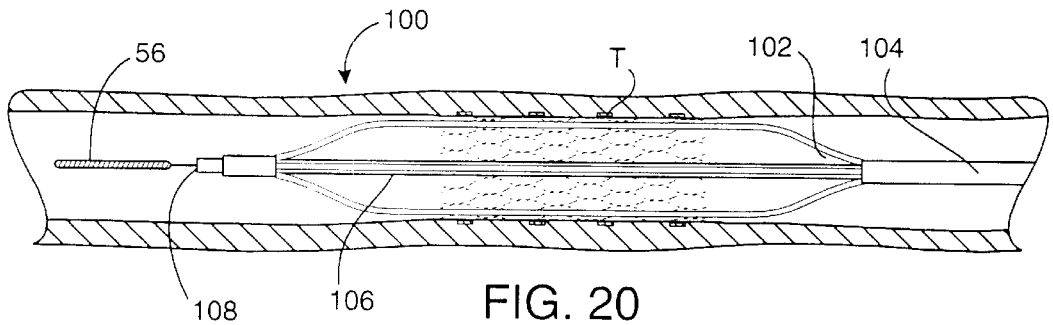
Figure 21:
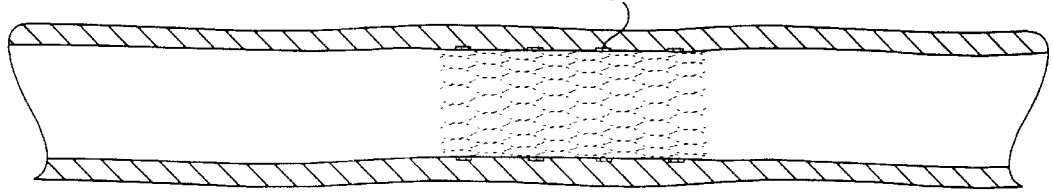

Referring now to FIG. 18, the cutting head 100 of the stenotic material removal mechanism is advanced from the inner catheter in the contracted position and positioned across the stenosis S within the stent T. The cutting head 100 is then expanded within the stenosis S, as shown in FIG. 19. The expansion may occur passively, by withdrawing the optional tubular sheath 58 (shown in FIG. 1) and allowing the resilient cutting blades 102 of the cutting head 100 to expand outward. Alternatively, the expansion may occur actively and controllably, by withdrawing the inner actuating member 106 to expand the cutting blades 102 outward and increase the width or diameter of the cutting head 100. The stenotic material removal mechanism is then activated by rotating the cutting head 100 to remove the stenotic material M from within the stenosis S. The cutting head 100 may be manually rotated by the operator or by a drive motor 72 within a motor drive unit 70, as shown in FIG. 1. Medications, chemicals, ionizing radiation or energy, such as electrical, magnetic, ultrasonic, hydraulic, pulsed hydraulic, laser or thermal energy may be applied to assist in removal of the stenotic material M and/or for denaturing the remaining tissue to discourage further restenosis at the treatment site. The stenotic material M that is removed may be aspirated out through the aspiration port 64 of the outer catheter 60 (shown in FIG. 1). The electrodes 116, 118 of the sensing means located on the cutting blades 102 monitor the proximity or contact between the cutting head 100 and the stent T. When the cutting blades 102 have approached close enough to the stent T to indicate effective recanalization of the stenosis S, as shown in FIG. 20, the stenotic material removal mechanism is deactivated. The catheter system is then withdrawn, leaving the stented region recanalized and open to renewed blood flow, as shown in FIG. 21.

Figure 22:
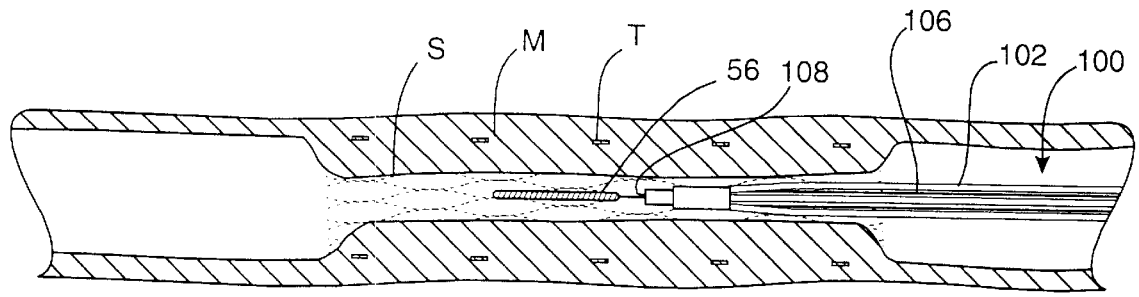
FIGS. 22, 23, 24 and 25 are a series of drawings illustrating an alternate method of the present invention using the apparatus of FIG. 2.

FIGS. 22, 23, 24 and 25 are a series of drawings illustrating an alternate method of the present invention. As above, the method is illustrated and described using the stenotic material removal mechanism of FIGS. 2–6, but the method may be applied using most of the various apparatus described above with minor modifications to the procedure. In this alternative method, the catheter carrying the stenotic material removal mechanism is positioned on one side of the restenosed stented region. The cutting head 100 of the stenotic material removal mechanism is extended from the catheter and advanced part-way into the stent T and the cutting blades 102 are expanded outward, as shown in FIG. 22. The electrodes 116, 118 of the sensing means located on the cutting blades 102 monitor the proximity or contact between the cutting head 100 and the stent T so that the diameter of the cutting head 100 can be accommodated to the internal diameter of the stent T. If the stenosis S does not extend all of the way to the end of the stent T, the expansion step can be performed while the cutting head 100 is stationary. However, if necessary, the stenotic material removal mechanism can be activated by rotating the cutting head 100 as the cutting blades 102 expand outward to begin removing the stenotic material M while adjusting the diameter of the cutting head 100 to the size of the stent T.

Figure 23:
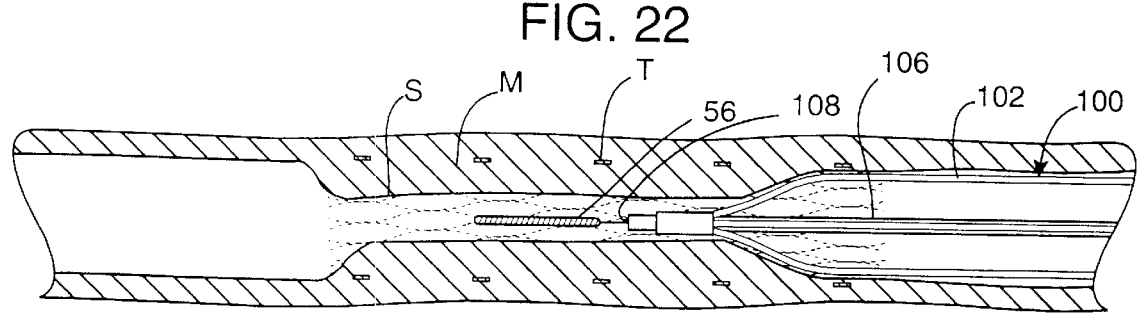
Figure 24:
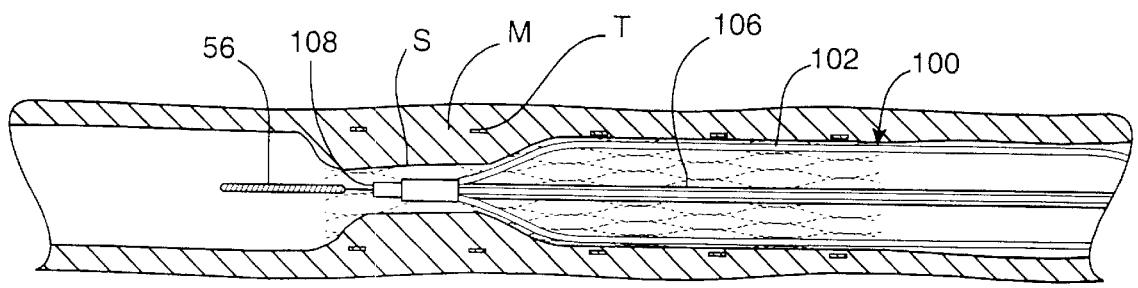
Figure 25:
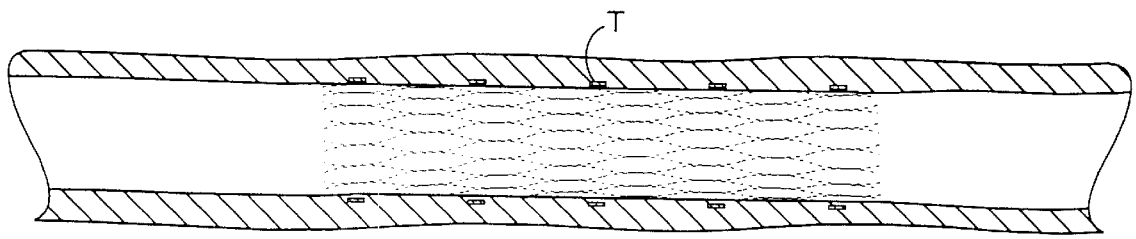

The stenotic material M is removed from within the stent T by rotating the cutting head 100 and advancing it through the stenosis S, as shown in FIGS. 23 and 24. The diameter of the cutting head 100 can be held constant as it is advanced through the stenosis S or it can be adjusted continuously based on feedback from the sensing means. Medications, chemicals, ionizing radiation or energy, such as electrical, magnetic, ultrasonic, hydraulic, pulsed hydraulic, laser or thermal energy may be applied to assist in removal of the stenotic material M and/or for denaturing the remaining tissue to discourage further restenosis at the treatment site. The stenotic material M that is removed may be aspirated out through the aspiration port 64 of the outer catheter 60 (shown in FIG. 1). When the cutting head 100 has passed all the way through the stenosis S, the stenotic material removal mechanism is deactivated and the catheter system is withdrawn, leaving the stented region recanalized and open to renewed blood flow, as shown in FIG. 25.

This method can be effectively performed in the reverse direction, by advancing the cutting head 100 all the way across the stenosis in a contracted or compressed state. The cutting head 100 is then expanded within the far end of the stenosis S or within the vessel beyond the stenosis, using the sensing means to adjust the diameter of the cutting head 100 to the size of the stent T. The cutting head 100 is then rotated while withdrawing it toward the catheter to advance it through the stenosis S.

Figure 26:
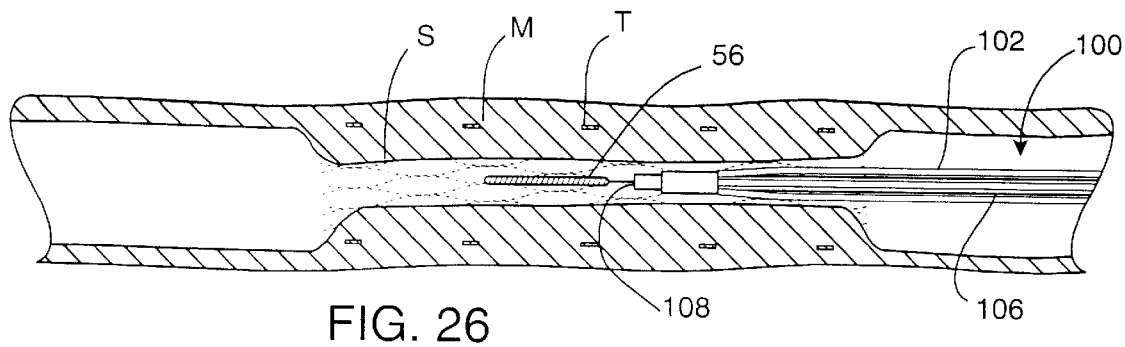
FIGS. 26, 27, 28 and 29 are a series of drawings illustrating another alternate method of the present invention using the apparatus of FIG. 2.
Figure 27:
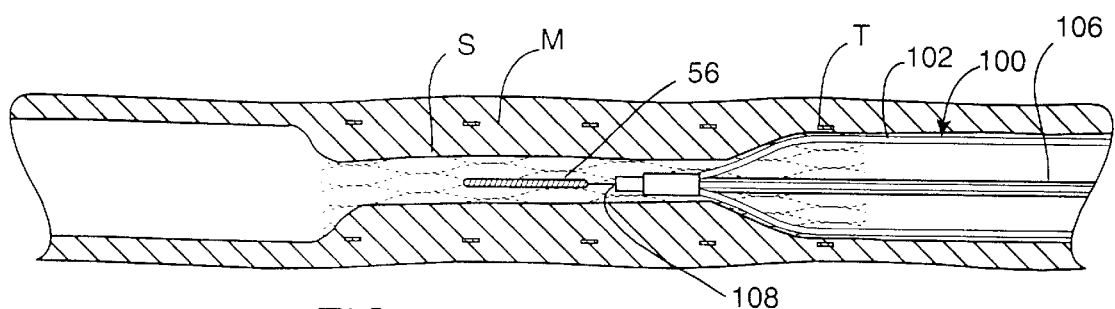
Figure 28:
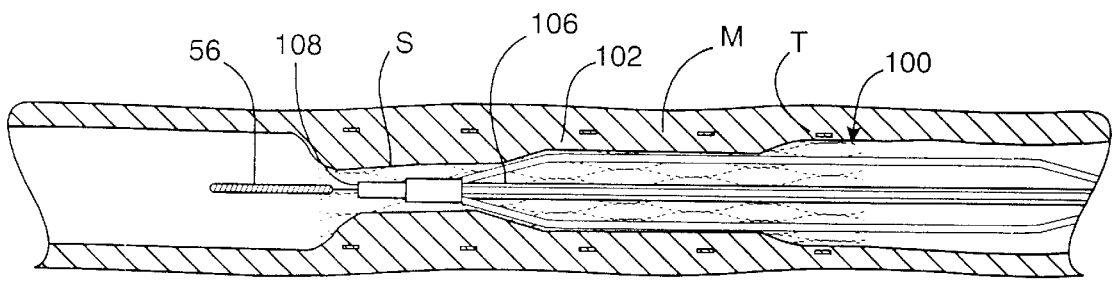
Figure 29:
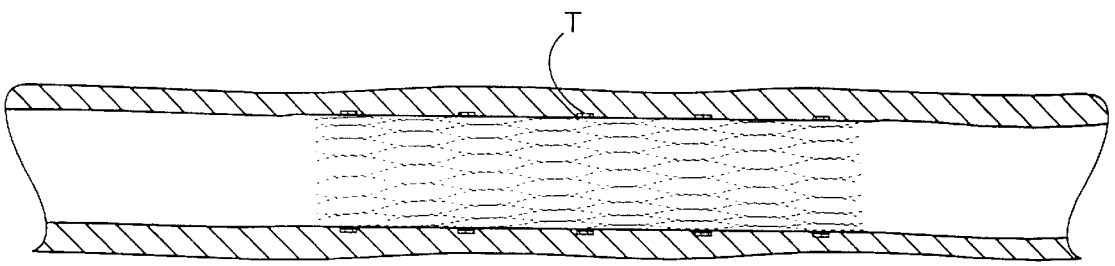

FIGS. 26, 27, 28 and 29 are a series of drawings illustrating another alternate method of the present invention. Once again, the method is illustrated and described using the stenotic material removal mechanism of FIGS. 2–6, but the method may be applied using most of the various apparatus described above with minor modifications to the procedure. In this alternative method, the catheter carrying the stenotic material removal mechanism is positioned on one side of the restenosed stented region. The cutting head 100 of the stenotic material removal mechanism is extended from the catheter and advanced part-way into the stenosis S within the stent T, as shown in FIG. 26. The cutting blades 102 are then expanded outward within the stenosis S, either passively or actively and controllably as described above, to increase the width or diameter of the cutting head 100. The stenotic material removal mechanism is then activated by rotating the cutting head 100 to begin removing the stenotic material M from within the stenosis S, as shown in FIG. 27. Medications, chemicals, ionizing radiation or energy, such as electrical, magnetic, ultrasonic, hydraulic, pulsed hydraulic, laser or thermal energy may be applied to assist in removal of the stenotic material M and/or for denaturing the remaining tissue to discourage further restenosis at the treatment site. The stenotic material M that is removed may be aspirated out through the aspiration port 64 of the outer catheter 60 (shown in FIG. 1). The electrodes 116, 118 of the sensing means located on the cutting blades 102 monitor the proximity or contact between the cutting head 100 and the stent T. When the cutting blades 102 have approached close enough to the stent T to indicate effective recanalization of that portion of the stenosis S, the cutting head 100 is advanced farther into the stenosis S, as shown in FIG. 28. The stenotic material removal mechanism may be deactivated and advanced step-wise into the stenosis S by contracting or compressing the cutting head 100, advancing it a short distance and expanding it again in a new portion of the stent T. Otherwise, the cutting head 100 may be advanced continuously, relying on either the resiliency of the cutting blades 102 or active control for adjusting the width or diameter of the cutting head 100 as it advances. When the sensing means indicates that the new portion of the stent T has been effectively recanalized, the cutting head 100 is advanced again along the stenosis S until the entire stented region has been recanalized, as shown in FIG. 29.

This method can be effectively performed in the reverse direction, by advancing the cutting head 100 all the way across the stenosis in a contracted or compressed state. The cutting head 100 is then expanded within the far end of the stenosis S or within the vessel beyond the stenosis, either passively or actively and controllably as described above, to increase the width or diameter of the cutting head 100. The cutting head 100 is then rotated while withdrawing it toward the catheter to advance it through the stenosis in either a step-wise or continuous fashion. Medications, chemicals, ionizing radiation or energy, such as electrical, magnetic, ultrasonic, hydraulic, pulsed hydraulic, laser or thermal energy may be applied to assist in removal of the stenotic material and/or for denaturing the remaining tissue to discourage further restenosis at the treatment site. The sensing means is used to monitor the proximity or contact between the cutting head 100 and the stent T in order to control the diameter and/or the rate of advancement of the cutting head 100 for effective recanalization of the stenosis S within the stent T.

Figure 30:
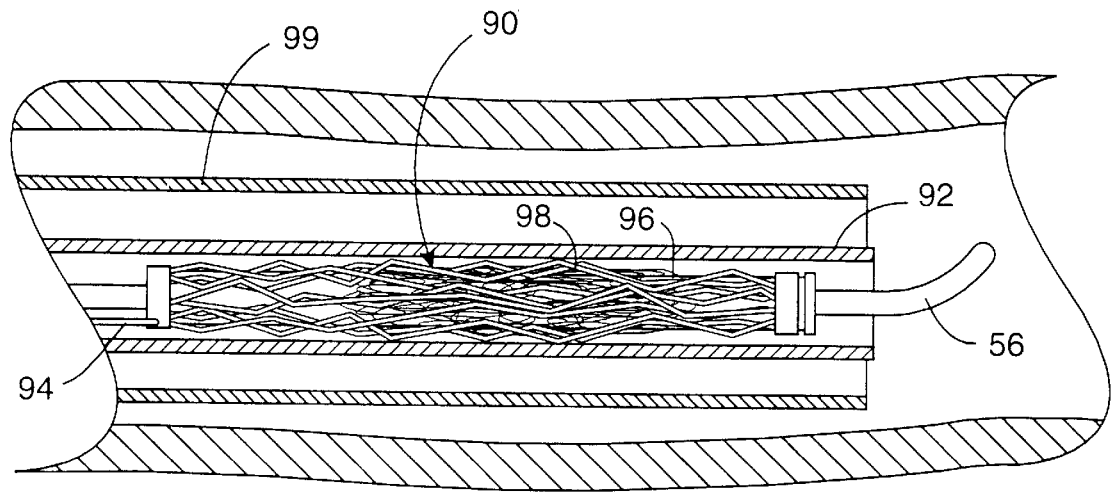
FIGS. 30, 31 and 32 are a series of drawings illustrating the operation of an optional embolic filter apparatus which may be used in conjunction with the method of the present invention.
Figure 31:
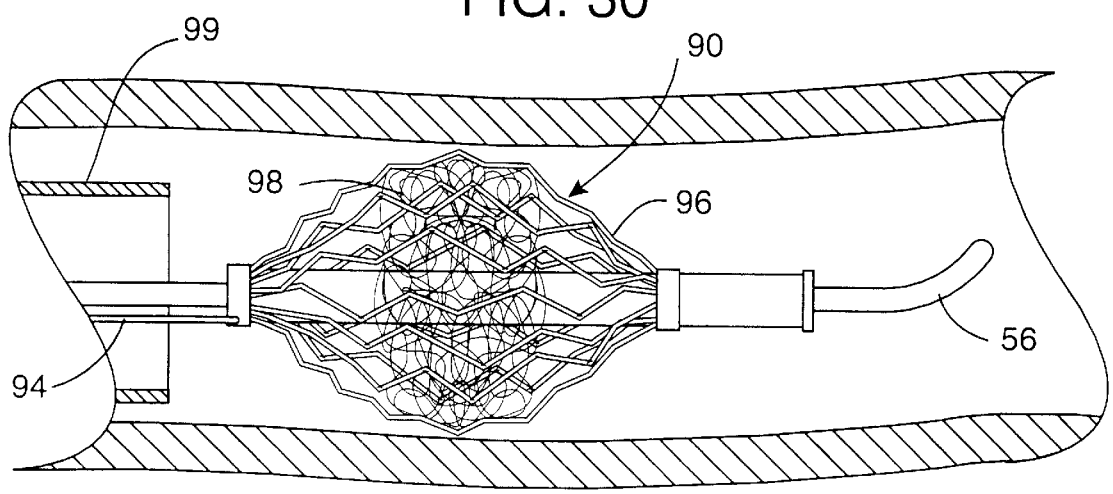
Figure 32:
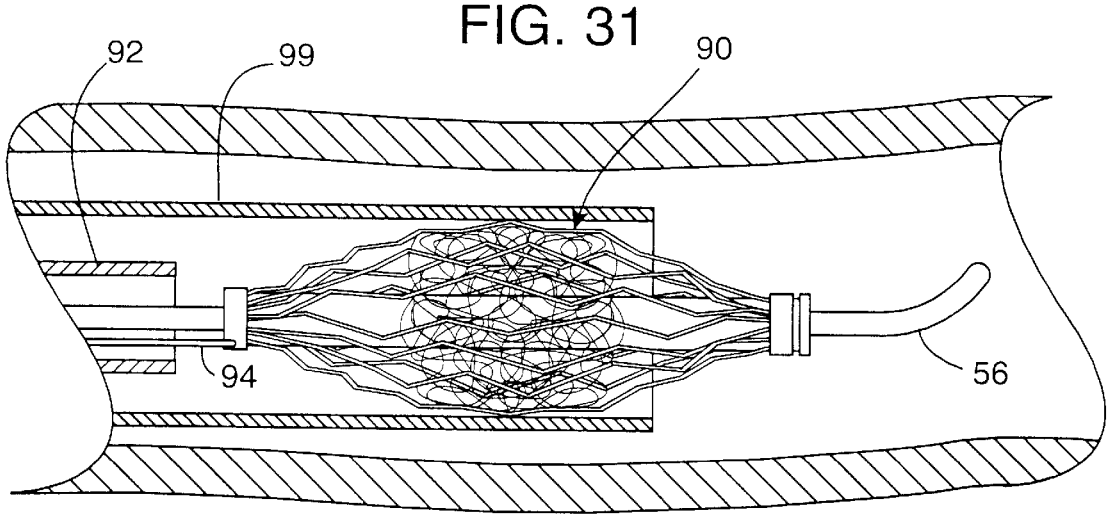

The methods of the present invention will optionally further comprise collecting and withdrawing the removed stenotic material from the blood vessel. FIGS. 30, 31 and 32 are a series of drawings illustrating the operation of an optional embolic filter apparatus 90 which may be used in conjunction with the method of the present invention. The embolic filter apparatus 90 may be arranged coaxially as part of the catheter system as shown in FIG. 1 and introduced through a single vascular access point and positioned distally to the treatment site. Alternatively, embolic filter apparatus 90 may be arranged on a separate catheter which is introduced through a different vascular access point and positioned proximally or distally to the treatment site.

In FIG. 30, the embolic filter 90 is shown in its compacted position within a tubular sheath 92 as it is first introduced into the vasculature and advanced to or across the stenosis. In coaxial arrangements, the tubular sheath 92 may be the same as the tubular sheath 58 or the inner catheter 50 of the catheter system of FIG. 1. The embolic filter 90 may be delivered coaxially over a separate guidewire 56, or it may be built integrally with a guidewire 56 constructed especially for the purpose. Once the embolic filter 90 is in position, the tubular sheath 92 is withdrawn and the embolic filter 90 is allowed to expand to the full diameter of the vessel, as shown in FIG. 31. The expansion can occur passively, or an actuation member 94 may be used to actively expand the embolic filter 90. The embolic filter 90 should be expandable over a range of approximately 2 mm to 5 mm for use in stented coronary arteries or as high as 6 mm for use in stented vein grafts and even larger for use in stented peripheral vessels and other stented body structures. The embolic filter 90 should contract to as small a diameter as possible for passing through tightly stenotic lesions, preferably to a diameter smaller than 2 mm, more preferably to a diameter smaller than 1 mm. The embolic filter 90 has a plurality of structural members 96, which enclose and support a nonthrombogenic expandable filter medium 98. The structural members 96 can be made of a metallic or polymeric material, and may be biased radially outward to assist in expansion of the embolic filter 90. The expandable filter medium 98 may be a porous foam material or it may be a fibrous filter medium such as polyester fiber, which, in its expanded state, has a pore size appropriate for capturing significant emboli which may be dislodged during the stenotic material removal process. The pore size of the expandable filter medium 98 may advantageously be in the range of 0.01 to 0.2 mm to capture potential emboli. Once the stenotic material removal procedure has been completed, the embolic filter 90 is compressed slightly, by passive or active means, and withdrawn into an outer catheter 99, to capture the emboli without releasing them, as shown in FIG. 32. In coaxial arrangements, the outer catheter 99 may be the inner catheter 50 or outer catheter 60 of the catheter system of FIG. 1. The outer catheter 99 and the embolic filter 90 are then withdrawn from the patient's vasculature. In other alternative methods, embolic filters and/or occlusion balloons may be placed upstream and downstream of the treatment site to isolate or capture potential emboli.

FIGS. 33, 34, 35 and 36 are a series of drawings illustrating a method and an apparatus according to the present invention that combine a stenotic material removal mechanism with an embolic filter for capturing stenotic material M which is removed from within the stent T. The apparatus has a cutting head 300 which is mounted on the distal end of an inner catheter shaft 302. The cutting head 300 has a cutting portion 304 and a filtering or material capturing portion 306. In this illustrative embodiment, the cutting portion 304 is centrally located on the cutting head 300 and the material capturing portion 306 is located distal to it. The cutting head 300 should be expandable over a range of approximately 2 mm to 5 mm for use in stented coronary arteries or as high as 6 mm for use in stented vein grafts and even larger for use in stented peripheral vessels and other stented body structures. The cutting head 300 should contract to as small a diameter as possible for passing through tightly stenotic lesions, preferably to a diameter smaller than 2 mm, more preferably to a diameter smaller than 1 mm. The effective cutting length of the cutting portion 304 is preferably within the range of approximately 10 mm to 40 mm for use in stented coronary arteries and can be longer for use in stented peripheral vessels. Additionally or alternatively, the cutting head 300 may also include a second material capturing portion 306' located proximally to the cutting portion 304. Alternatively, the material capturing portion 306 may occupy the entire length of the cutting head 300. The cutting portion 304 of the cutting head 300 may take any one of the different forms described herein in connection with the various embodiments of the invention. For illustrative purposes, the cutting portion 304 is shown having a plurality of longitudinally oriented cutting blades 308, similar to those shown in FIGS. 2–6. Alternatively, the cutting blades may be laterally or circumferentially oriented or helically configured, similar to those shown in FIGS. 7–10, or any convenient geometry. The cutting blades 308 of the cutting head 300 may be either passively or actively expandable, as described above.

The material capturing portion 306 preferably contains a nonthrombogenic expandable filter medium 310. The expandable filter medium 310 may be a porous foam material or it may be a fibrous filter medium such as polyester fiber, which, in its expanded state, has a pore size appropriate for capturing significant emboli which may be dislodged during the stenotic material removal process. The pore size of the expandable filter medium 310 may advantageously be in the range of 0.01 to 0.2 mm to capture potential emboli. The expandable filter medium 310 is enclosed and supported by the cutting blades 308 of the cutting head 300. Additionally or alternatively, the expandable filter medium 310 may include a membranous filter material that is attached to and suspended between the cutting blades 308 of the cutting head 300. Suitable membranous filter materials include flexible woven, nonwoven or knitted filtration fabrics. The expandable filter medium 310 occupies a distal portion 306 and/or a proximal portion 306' of the cutting head 300. Alternatively, the expandable filter medium 310 may occupy the entire length of the cutting head 300.

Figure 33:
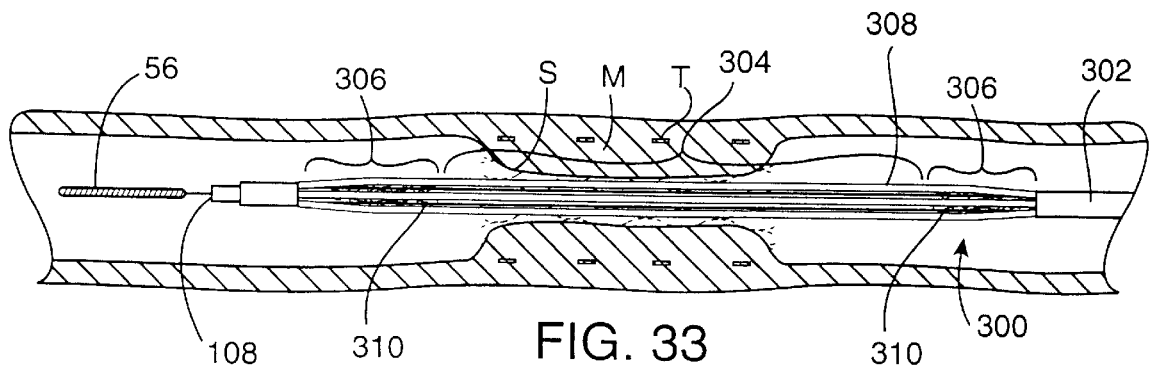
FIGS. 33, 34, 35 and 36 are a series of drawings illustrating the operation of a combined stenotic material removal mechanism and stenotic material capture mechanism according to the present invention.
Figure 34:
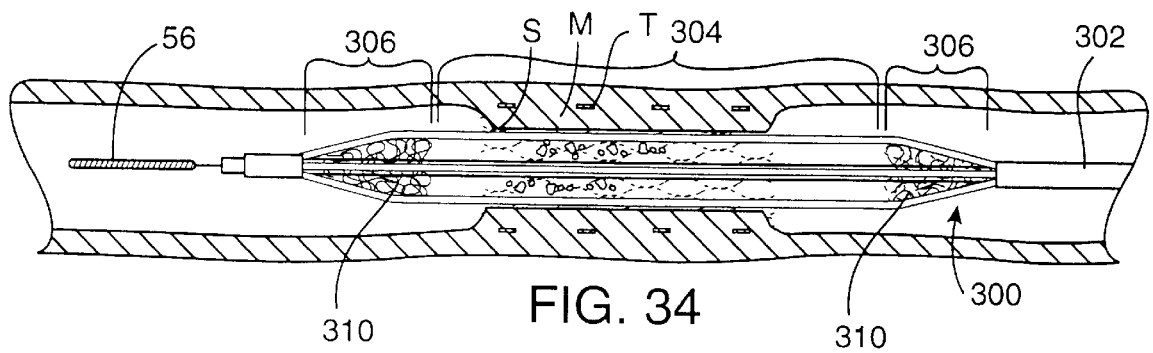
Figure 35:
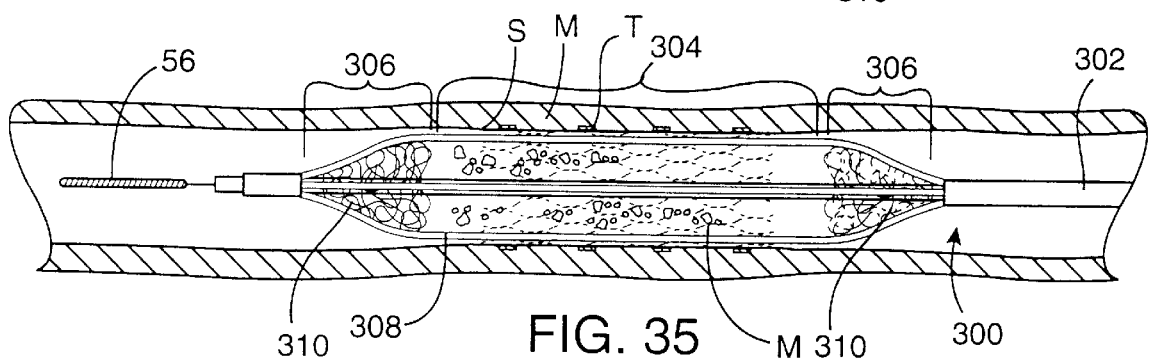

In use, the catheter carrying the stenotic material removal mechanism is positioned on one side of the restenosed stented region. The cutting head 300 is extended from the catheter and advanced across the stenosis S in the contracted position, as shown in FIG. 33. The expandable filter medium 310 is compressed within the cutting head 300. The cutting head 300 is then expanded within the stenosis S, as shown in FIG. 34. The expansion may occur passively, by withdrawing a surrounding tubular sheath 58 (shown in FIG. 1) and allowing the resilient cutting blades 308 of the cutting head 300 to expand outward. Alternatively, the expansion may occur actively and controllably, by operating an actuating mechanism to expand the cutting blades 308 outward and increase the width or diameter of the cutting head 300, as described above in connection with FIGS. 2–6. Preferably, the filter medium 310 within the material capturing portion 306 of the cutting head 300 expands to a diameter at least as large or larger than the expanded diameter of the cutting portion 304 of the cutting head 300. The stenotic material removal mechanism is then activated by rotating the cutting head 300 to remove the stenotic material M from within the stenosis S. The cutting head 300 may be rotated manually by the operator or by a drive motor 72 within a motor drive unit 70, as shown in FIG. 1. Medications, chemicals, ionizing radiation or energy, such as electrical, magnetic, ultrasonic, hydraulic, pulsed hydraulic, laser or thermal energy may be applied to assist in removal of the stenotic material M and/or for denaturing the remaining tissue to discourage further restenosis at the treatment site. The stenotic material M that is removed is captured by the filter medium 310 within the material capturing portion 306 of the cutting head 300, as shown in FIG. 35.

Figure 36:
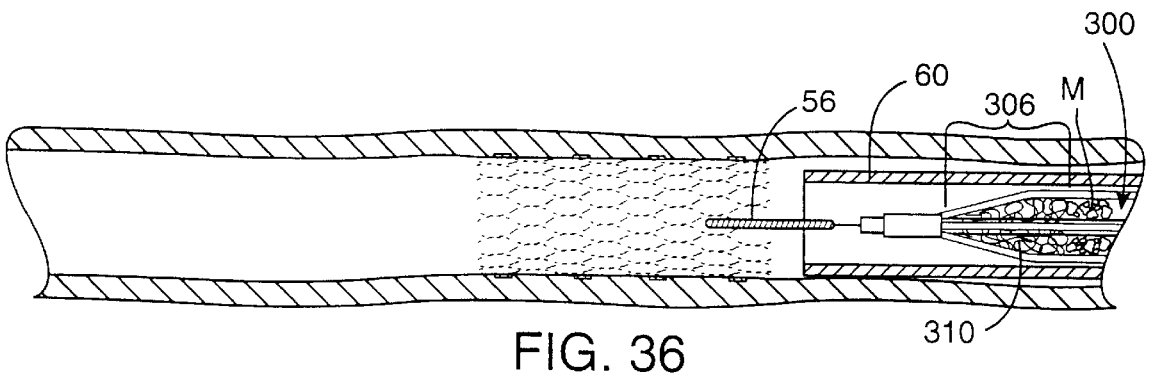

Preferably, the cutting head 300 includes a sensing means, such as the sensor electrodes 116, 118 described above in connection with FIGS. 5 and 6, for sensing the proximity or contact between the cutting blades 308 of the cutting head 300 and the stent T. When the cutting blades 308 have approached close enough to the stent T to indicate effective recanalization of the stenosis S, as shown in FIG. 35, the stenotic material removal mechanism is deactivated. The cutting head 300 and all of the stenotic material M captured by the filter medium 310 within the material capturing portion 306 of the cutting head 300 are then withdrawn into the outer catheter 60, as shown in FIG. 36. The catheter system is then withdrawn from the patient, leaving the stented region recanalized and open to renewed blood flow.

Alternatively, this cutting head 300 with a combined stenotic material removal mechanism and stenotic material capture mechanism may be operated as a simple shearing body without a sensing means. In this alternative method, the cutting head 300 may be rotated and/or translated within the stenosis S to dislodge stenotic material M from within an interface envelope defined by the stent T embedded within the vessel wall, as shown in FIG. 34. The cutting head 300 may be expanded passively or actively to remove all of the stenotic material M from within the stent T. The stenotic material M that is removed is captured by the filter medium 310 within the material capturing portion 306 of the cutting head 300, as shown in FIG. 35. The cutting head 300 and all of the stenotic material M captured by the filter medium 310 within the material capturing portion 306 of the cutting head 300 are then withdrawn into the outer catheter 60, as shown in FIG. 36.

Figure 37:
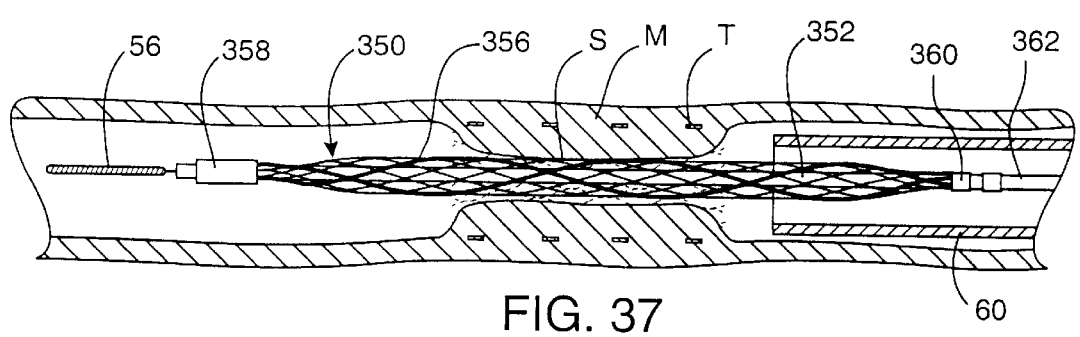
FIGS. 37, 38 and 39 are a series of drawings illustrating the operation of an alternate combined stenotic material removal mechanism and stenotic material capture mechanism according to the present invention.
Figure 38:
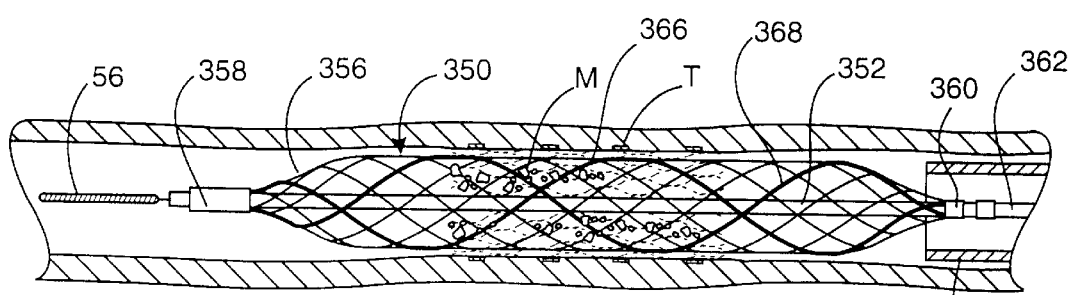
Figure 39:
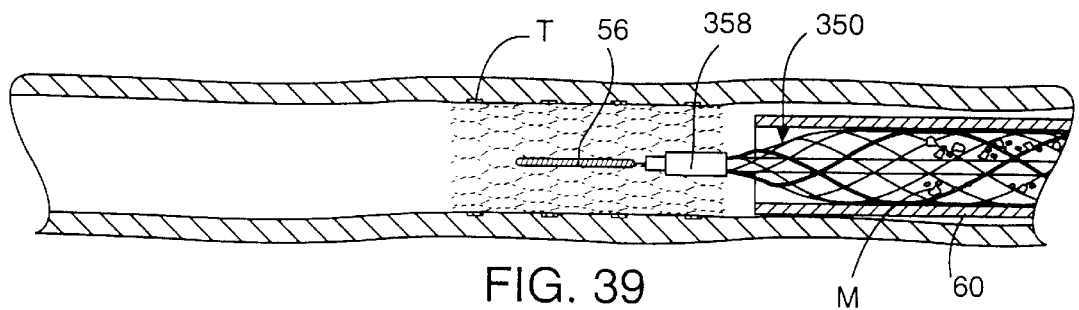

FIGS. 37, 38 and 39 are a series of drawings illustrating an alternate method and apparatus according to the present invention that also combine a stenotic material removal mechanism with a means for capturing the stenotic material M that is removed from within the stent T. The apparatus has a head 350 which is mounted on the distal end of an inner catheter shaft 352. The head 350 is a cage-like structure of counterwound or interwoven helical elements 356. The helical elements 356 may comprise round filaments, ribbon filaments, or the like, made of a metallic or polymeric material. The helical elements 356 are attached to a distal ring 358 and to a proximal ring 360 which is free to slide over the inner catheter shaft 352. The helical elements 356 may be treated by coldworking or heat treatment to have an elastic memory so that they are biased toward the expanded position, allowing the head 350 to be passively expanded. Alternatively, the proximal ring 360 may optionally be attached to a rod, sleeve, or other means 362 for axially translating the proximal ring 360 to actively and controllably adjust the radius of the head 350. The cage-like structure of counterwound or interwoven helical elements 356 serves to capture dislodged stenotic material M that passes through the interstices between the helical elements 356.

In use, the catheter 60 carrying the stenotic material removal mechanism is positioned on one side of the restenosed stented region. The head 350 is extended from the catheter and advanced across the stenosis S in a contracted position, as shown in FIG. 37. The head 350 is then expanded within the stenosis S, either passively or actively and controllably as described above. The stenotic material removal mechanism is then activated by rotating and/or translating the head 350 within the stenosis S to remove stenotic material M from within the stent T, as shown in FIG. 38. The head 350 may be rotated manually by the operator or by a drive motor 72 within a motor drive unit 70, as shown in FIG. 1. The head 350 may operate by cutting action, abrasive action or shearing action. Alternatively or additionally, medications, chemicals, ionizing radiation or energy, such as electrical, magnetic, ultrasonic, hydraulic, pulsed hydraulic, laser or thermal energy may be applied to assist in removal of the stenotic material M and/or for denaturing the remaining tissue to discourage further restenosis at the treatment site. The stenotic material M that is dislodged passes through the interstices between the helical elements 356 and is captured within the cage-like structure of the head 350.

Preferably, the head 350 includes a sensing means for sensing the proximity or contact between the helical elements 356 of the head 350 and the stent T. As shown in FIG. 38, the sensing means may take the form of one or more sensor electrode wires 366, 368 interwoven among the helical elements 356 of the head 350. Alternatively, the helical elements 356 of the head 350 may serve as sensor electrodes themselves. When the helical elements 356 of the head 350 have approached close enough to the stent T to indicate effective recanalization of the stenosis S, as shown in FIG. 38, the stenotic material removal mechanism is deactivated. The head 350 and all of the stenotic material M captured within the cage-like structure of the helical elements 356 are then withdrawn into the outer catheter 60, as shown in FIG. 39. The interstices between the helical elements 356 of the head 350 contract as the head 350 is drawn into the catheter 60, helping to assure that the particles of dislodged stenotic material M remain captured within the catheter. The catheter system is then withdrawn from the patient, leaving the stented region recanalized and open to renewed blood flow.

Alternatively, the head 350 of this apparatus may be operated as a simple shearing body without a sensing means. In this alternative method, the head 350 may be rotated and/or translated within the stenosis S to dislodge stenotic material M from within an interface envelope defined by the stent T embedded within the vessel wall, as shown in FIG. 38. The head 350 may be expanded passively or actively to remove all of the stenotic material M from within the stent T. The stenotic material M that is dislodged passes through the interstices between the helical elements 356 and is captured within the cage-like structure of the head 350. The head 350 and all of the stenotic material M captured within it are then withdrawn into the outer catheter 60, as shown in FIG. 39.

Figure 40:
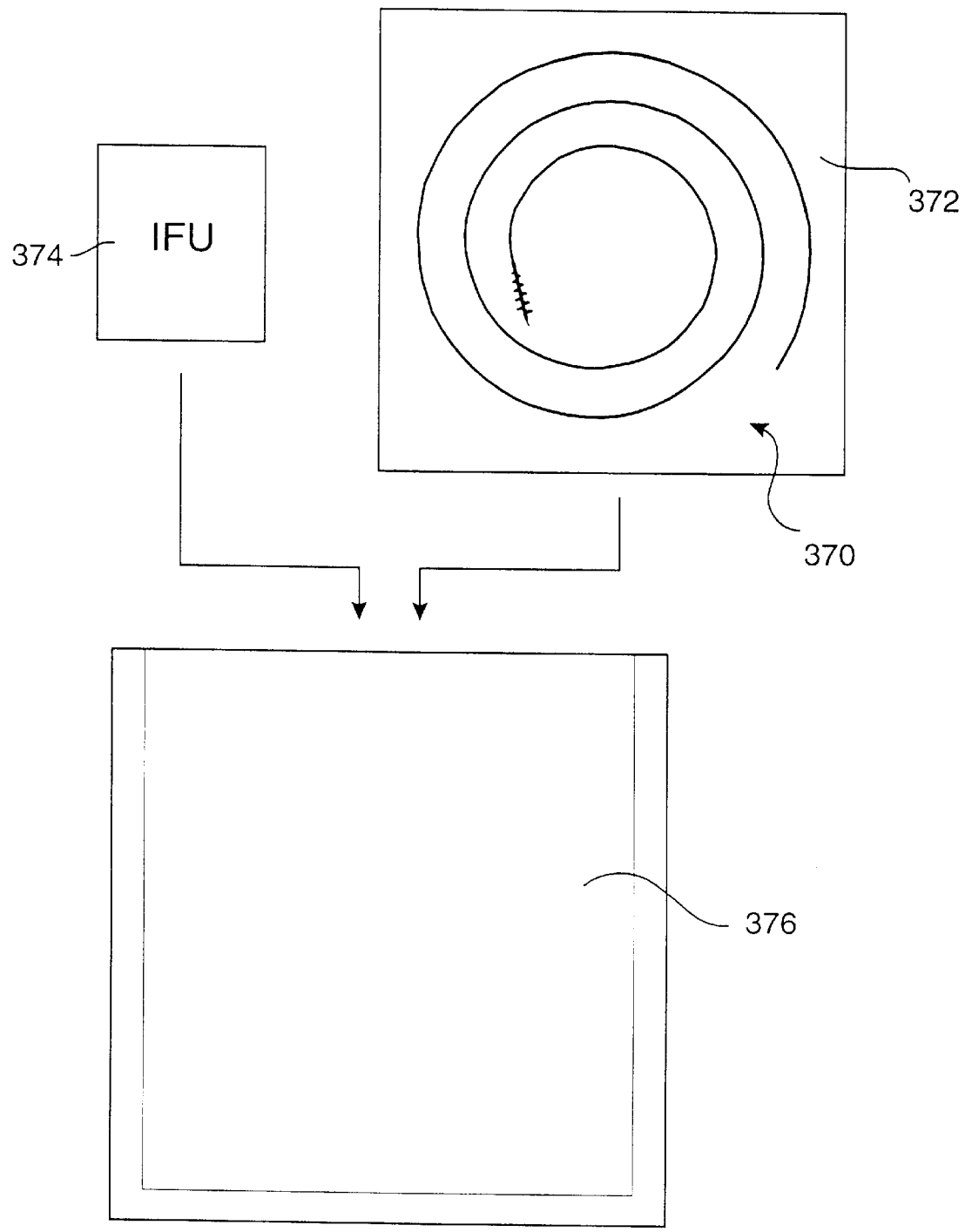
FIG. 40 illustrates a kit including a catheter, a package and instructions for use according to the present invention.

Referring now to FIG. 40, a catheter kit according to the present invention comprises a catheter or catheter system 370, often mounted on a board or in a tray 372, instructions for use (IFU) 374, and a pouch 376 or other conventional package. A motor drive unit 70 (FIG. 1) may be packaged together with the catheter kit or separately. The instructions for use (IFU) 374 are typically part of a separate sheet or booklet which together with the catheter 370, is packaged within the pouch 376 or other packaging material. The packaging and its contents will preferably be sterile or sterilizable. The instructions for use (IFU) 374 will set forth method steps comprising the method(s) as described above.

Although the method of the present invention has been described using the example of revascularizing restenosed coronary arteries, it should be noted that the methods and apparatus disclosed may be used for reopening any previously stented body passage which has been subject to restenosis or reclosure. Other body passages where these methods and apparatus may apply include the peripheral blood vessels, the urinary tract, the digestive tract and the respiratory tract.

What is claimed is:

1. A method for removing stenotic material from within a stent located within a body vessel, said method comprising:
   operating a stenotic material removal mechanism to remove stenotic material from within the stent;
   sensing proximity or contact between said stenotic material removal mechanism and the stent using a non-imaging sensor; and
   determining an appropriate endpoint for removal of stenotic material from within the stent based on the sensed proximity or contact between said stenotic material removal mechanism and the stent for effective recanalization of the body vessel.

2. The method of claim 1 further comprising controlling a depth to which said stenotic material removal mechanism removes the stenotic material from within the stent.

3. The method of claim 1 comprising diametrically expanding said stenotic material removal mechanism.

4. The method of claim 1 comprising directing said stenotic material removal mechanism to remove stenotic material from a selected area within the stent.

5. The method of claim 1 further comprising producing a signal indicative of the proximity or contact between said stenotic material removal mechanism and the stent.

6. The method of claim 1 further comprising deactivating said stenotic material removal mechanism when a predetermined level of proximity or contact between said stenotic material removal mechanism and the stent is detected.

7. The method of claim 1 further comprising monitoring the proximity or contact between said stenotic material removal mechanism and the stent.

8. The method of claim 7 wherein said sensor means comprises at least one electrical conductor on an exterior of said stenotic material removal mechanism and wherein the step of monitoring comprises detecting a leakage current when said at least one electrical conductor contacts the stent.

9. The method of claim 7 wherein said sensor means comprises a first electrical conductor and a second electrical conductor on an exterior of said stenotic material removal mechanism and wherein the step of monitoring comprises detecting a leakage current when said first electrical conductor and said second electrical conductor contacts the stent.

10. The method of claim 7 wherein said sensor means comprises at least one electrical conductor positioned on said stenotic material removal mechanism and wherein the step of monitoring comprises detecting a change in electrical impedance when said at least one electrical conductor approaches the stent.

11. The method of claim 7 wherein said sensor means comprises a first electrical conductor and a second electrical conductor positioned on said stenotic material removal mechanism and wherein the step of monitoring comprises detecting a change in electrical impedance when said first electrical conductor and said second electrical conductor approach the stent.

12. The method of claim 1 further comprising aspirating stenotic material removed from within the stent.

13. The method of claim 1 further comprising collecting stenotic material removed from within the stent.

14. The method of claim 1 further comprising inserting said stenotic material removal mechanism into the body vessel on an elongated catheter.

15. The method of claim 14 further comprising introducing said stenotic material removal mechanism on said elongated catheter into the body vessel through a percutaneous puncture.

16. A method for removing stenotic material from within a stent located within a body vessel, said method comprising:

engaging a stenotic material removal mechanism to remove a portion of stenotic material from within the stent;

expanding the stenotic material removal mechanism to remove additional portions of the stenotic material; and limiting the expansion of the stenotic material removal mechanism when or before the stenotic material removal mechanism engages the stent.

17. The method of claim 16 comprising diametrically expanding said stenotic material removal mechanism.

18. The method of claim 16 further comprising deactivating said stenotic material removal mechanism when or before the stenotic material removal mechanism engages the stent.

19. The method of claim 16 further comprising directing said stenotic material removal mechanism to remove stenotic material from a selected area within the stent.

20. The method of claim 16 further comprising sensing proximity or contact between said stenotic material removal mechanism and the stent.

21. The method of claim 20 further comprising deactivating said stenotic material removal mechanism when a predetermined level of proximity or contact between said stenotic material removal mechanism and the stent is detected.

22. The method of claim 16 further comprising aspirating stenotic material removed from within the stent.

23. The method of claim 16 further comprising collecting stenotic material removed from within the stent.

24. The method of claim 16 further comprising inserting said stenotic material removal mechanism into the body vessel on an elongated catheter.

25. The method of claim 24 further comprising introducing said stenotic material removal mechanism on said elongated catheter into the body vessel through a percutaneous puncture.

* * * * *